US012617775B2

(12) United States Patent
Kostik et al.

(10) Patent No.: US 12,617,775 B2
(45) Date of Patent: *May 5, 2026

(54) PROCESSES OF MAKING CSF-1R INHIBITORS AND METHODS OF USE THEREOF

(71) Applicant: Deciphera Pharmaceuticals, LLC, Waltham, MA (US)

(72) Inventors: Elena Kostik, Waltham, MA (US); Ann Gelormini, Waltham, MA (US); Michael D. Kaufman, Waltham, MA (US)

(73) Assignee: Deciphera Pharmaceuticals, LLC, Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/299,605

(22) Filed: Aug. 14, 2025

(65) Prior Publication Data

US 2025/0368622 A1 Dec. 4, 2025

Related U.S. Application Data

(63) Continuation of application No. PCT/US2025/027041, filed on Apr. 30, 2025.

(60) Provisional application No. 63/641,022, filed on May 1, 2024.

(51) Int. Cl.
*C07D 401/14* (2006.01)
*B01J 31/24* (2006.01)

(52) U.S. Cl.
CPC ........ *C07D 401/14* (2013.01); *B01J 31/2409* (2013.01); *B01J 2231/34* (2013.01); *B01J 2531/004* (2013.01); *B01J 2531/824* (2013.01)

(58) Field of Classification Search
CPC ..... C07D 401/14; B01J 31/00; B01J 2231/00; B01J 2531/00; C07B 2200/00
See application file for complete search history.

(56) References Cited

U.S. PATENT DOCUMENTS

| | | | |
|---|---|---|---|
| 7,144,911 B2 | 12/2006 | Flynn et al. | |
| 7,202,257 B2 | 4/2007 | Flynn et al. | |
| 7,279,576 B2 | 10/2007 | Flynn et al. | |
| 7,342,037 B2 | 3/2008 | Flynn et al. | |
| 7,531,566 B2 | 5/2009 | Flynn et al. | |
| 7,666,895 B2 | 2/2010 | Flynn et al. | |
| 7,737,283 B2 | 6/2010 | Flynn et al. | |
| 7,790,756 B2 | 9/2010 | Flynn et al. | |
| 7,897,762 B2 | 3/2011 | Flynn et al. | |
| 8,143,293 B2 | 3/2012 | Flynn et al. | |
| 8,163,756 B2 | 4/2012 | Flynn et al. | |
| 8,188,113 B2 | 5/2012 | Flynn et al. | |
| 8,278,331 B2 | 10/2012 | Flynn et al. | |
| 8,461,179 B1 | 6/2013 | Flynn et al. | |
| 8,486,951 B2 | 7/2013 | Flynn et al. | |
| 8,569,319 B2 | 10/2013 | Flynn et al. | |
| 8,586,565 B2 | 11/2013 | Flynn et al. | |
| 8,637,672 B2 | 1/2014 | Flynn et al. | |
| 8,741,911 B2 | 6/2014 | Allgeier et al. | |
| 8,921,565 B2 | 12/2014 | Flynn et al. | |
| 8,940,756 B2 | 1/2015 | Flynn et al. | |
| 9,012,635 B2 | 4/2015 | Flynn et al. | |
| 9,133,183 B2 | 9/2015 | Flynn et al. | |
| 9,181,223 B2 | 11/2015 | Kaufman et al. | |
| 9,187,474 B2 | 11/2015 | Flynn et al. | |
| 9,193,719 B2 | 11/2015 | Flynn et al. | |
| 9,309,224 B2 | 4/2016 | Flynn et al. | |
| 9,334,267 B2 | 5/2016 | Flynn et al. | |
| 9,382,228 B2 | 7/2016 | Flynn et al. | |
| 9,387,202 B2 | 7/2016 | Flynn et al. | |
| 9,457,019 B2 | 10/2016 | Flynn et al. | |
| 11,103,507 B2 | 8/2021 | Flynn et al. | |
| 11,679,110 B2 | 6/2023 | Flynn et al. | |
| 12,285,430 B2 | 4/2025 | Flynn et al. | |
| 12,447,149 B2 * | 10/2025 | Hamed .................. | A61K 47/32 |
| 2008/0214544 A1 | 9/2008 | Bellon et al. | |
| 2008/0255155 A1 | 10/2008 | Raeppel et al. | |
| 2010/0120806 A1 | 5/2010 | Flynn et al. | |
| 2010/0166699 A1 | 7/2010 | Thompson et al. | |
| 2011/0053906 A1 | 3/2011 | Huck et al. | |
| 2014/0145025 A1 | 5/2014 | Fang et al. | |
| 2015/0073129 A1 | 3/2015 | Herting et al. | |
| 2019/0091217 A1 | 3/2019 | Flynn et al. | |
| 2020/0129489 A1 | 4/2020 | Flynn et al. | |
| 2020/0352920 A1 | 11/2020 | Flynn et al. | |
| 2020/0354346 A1 | 11/2020 | Flynn et al. | |
| 2020/0354352 A1 | 11/2020 | Flynn et al. | |

(Continued)

FOREIGN PATENT DOCUMENTS

| | | |
|---|---|---|
| CN | 105120864 A | 12/2015 |
| CN | 105473617 A | 4/2016 |
| CN | 113880812 A | 1/2022 |

(Continued)

OTHER PUBLICATIONS

Brahmi, M. et al., Current Systemic Treatment Options for Tenosynovial Giant Cell Tumor/Pigmented Villonodular Synovitis: Targeting the CSF1/CSFIR Axis, Curr. Treat. Options in Oncol., 17:10 (2016).
El-Gamal, M. I. et al., Recent Advances of Colony-Stimulating Factor-1 Receptor (CSF-1R) Kinase and Its Inhibitors, J. Med. Chem., 61:5450-5466 (2018).
International Search Report and Written Opinion for International Patent Application No. PCT/US2019/068311 mailed Jul. 2, 2020.
PCT/US2024/058988 International Search Report and Written Opinion dated Mar. 24, 2025.
PCT/US2025/027041 International Search Report and Written Opinion mailed Sep. 19, 2025, 17 pages.
Silverman R.B. et al. Lead Discovery, The Organic Chemistry of Drug Design and Drug Action, 3rd Ed, Chapter 2, pp. 19-122, Elsevier (2014).

(Continued)

*Primary Examiner* — Theodore R. Howell
(74) *Attorney, Agent, or Firm* — Goodwin Procter LLP

(57) ABSTRACT

The present disclosure relates to processes of making a compound represented by Formula (I) and methods of use thereof.

8 Claims, No Drawings

(56) References Cited

U.S. PATENT DOCUMENTS

| | | | |
|---|---|---|---|
| 2021/0015801 | A1 | 1/2021 | Flynn et al. |
| 2023/0414614 | A1 | 12/2023 | Flynn et al. |

FOREIGN PATENT DOCUMENTS

| | | | |
|---|---|---|---|
| CN | 116283919 | A | 6/2023 |
| EA | 200802129 | A1 | 4/2009 |
| EP | 3632906 | A1 | 4/2020 |
| EP | 3632907 | A1 | 4/2020 |
| EP | 3682881 | A1 | 7/2020 |
| JP | 6364472 | B2 | 7/2018 |
| RU | 2330024 | C2 | 7/2008 |
| WO | WO-2003/000660 | A1 | 1/2003 |
| WO | WO-2008/079291 | A2 | 7/2008 |
| WO | WO-2010051373 | | 5/2010 |
| WO | WO-2014145015 | | 9/2014 |
| WO | WO-2014145023 | A1 | 9/2014 |
| WO | WO-2014145025 | | 9/2014 |
| WO | WO-2014145028 | | 9/2014 |
| WO | WO-2020139828 | A1 | 7/2020 |
| WO | WO-2022247786 | A1 | 12/2022 |

OTHER PUBLICATIONS

"Deciphera Pharmaceuticals Announces Positive, Preliminary, Top-Line Clinical Data for the Ongoing Phase 1 Clincial Study with DCC-3014 and an Update on Future Development Plans," 2019, 1-3.

"History of Changes for Study: NCT03069469 Study of DCC-3014 in Patients with Advanced Malignancies," ClinicalTrials.gov Archive, 2018, 1-5.

Al-Muhsen et al., "The Expression of Stem Cell Factor and c-Kit Receptor in Human Asthmatic Airways," Clinical and Experimental Allergy, 2004, 34: 911-917.

Attoub et al., "The C-Kit Tyrosine Kinase Inhibitor STI571 for Colorectal Cancer Therapy," Cancer Research, 2002, 62: 4879-4883.

Blay, JY et al., "P63: Patient-Reported Outcomes Following Treatment with Vimseltinib for Tenosynovial Giant Cell Tumour in a Phase 2 Expansion Study", Value in Health, Elsevier, Amsterdam, NL, vol. 25, No. 12 (Dec. 1, 2022), XP087229982.

Boisson et al., "c-Kit and c-kit mutations in mastocytosis and other hematological diseases," Journal of Leukocyte Biology, 2000, 67(2):135-148.

Brinkmann et al., "Fingolimod (FTY720): Discovery and Development of an Oral Drug to Treat Multiple Sclerosis," Nature Reviews | Drug Discovery, 2010, 9: 883-897.

Brunton et al., "Chemotherapy of Neoplastic Diseases," in, Goodman and Gilman's: The Pharmacological Basis of Therapeutics, 2008, 11th ed.: 853-908.

Burns et al., "C-FMS Inhibitors: A Patent Review," Expert Opinion on Therapeutic Patents, 2011, 147-165.

Caira M. R. et al. "Crystalline Polymorphism of Organic Compounds", Design of Organic Solids. Topics in Current Chemistry, vol. 198, p. 163-208 (1998).

Caldwell, T. M. et al., "Discovery of vimseltinib (DCC-3014), a highly selective CSF1R switch-control kinase inhibitor, in clinical development for the treatment of Tenosynovial Giant Cell Tumor (TGCT)," Biorg. Med. Chem. Lett. 74, (2022) 128928, 7 pages.

Carvajal et al., "KIT as a Therapeutic Target in Metastatic Melanoma," Journal of the American Medical Association, 2011, 305(22): 2327-2334.

Dewar et al., "Inhibition of c-fms by Imatinib: expanding the spectrum of treatment," Cell Cycle, 2005, 4(7):851-853.

Dewar et al., "Macrophage Colony-Stimulating Factor Receptor C-Fms is a Novel Target of Imatinib," Blood, 2005, 105(8): 3127-3132.

Di Lorenzo et al., "Expression of Proto-Oncogene C-Kit in High Risk Prostate Cancer," European Journal of Surgical Oncology, 2004, 30: 987-992.

Dorwald, "Side Reactions in Organic Synthesis," Wiley: VCH Weinhem Preface, 2005, 1-15 & 8: 279-308.

El Agamy et al., "Targeting c-Kit in the Therapy of Mast Cell Disorders: Current Update," European Journal of Pharmacology, 2012, 690: 1-3.

Fang Z. et al. Conformational restriction: an effective tactic in 'follow-on'-based drug discovery, Fugure Med Chem. 2014, 6(8): 885-901.

Fine et al., "Neoplasms of the Central Nervous System," Cancer Principles & Practice of Oncology, 2005, 1834-1887.

Fogarty et al., "Development of Protein Kinase Activators: AMPK as a Target in Metabolic Disorders and Cancer," Biochimica et Biophysica Acta, 2010, 1804: 581-591.

Gelderblom, H. et al., " 475P: Safety and Efficacy of Vimseltinib in Tenosynovial Giant Cell Tumour (TGCT)): Long-term Phase | Update", Annals of Oncology, vol. 33, (Sep. 1, 2022), page S757, XP093241096.

Gelderblom, H. et al., "Vimseltinib versus placebo for tenosynovial giant cell tumour (MOTION): a multicentre, randomised, double-blind, placebo-controlled, phase 3 trial", The Lancet, vol. 403, No. 10445, (Jun. 3, 2024), pp. 2709-2719, XP093241015.

Girouard et al., "Neurovascular Coupling in the Normal Brain and in Hypertension, Stroke, and Alzheimer Disease," J. Appl Physiol., 2006, 100: 328-335.

Gupta et al., "IL-3 Inhibits Human Osteoclastogenesis and Bone Resorption through Downregulation of c-Fms and Diverts the Cells to Dendritic Cell Lineage," The Journal of Immunology, 2010, 2261-2272.

Heinrich et al., "Inhibition of c-kit receptor tyrosine kinase activity by STI 571, a selective tyrosine kinase inhibitor," Blood, 2000, 96(3):925-932.

Henriksen et al., "Assessment of Osteoclast Number and Function: Application in the Development of New and Improved Treatment Modalities For Bone Diseases," Osteoporosis International, 2006, 18: 681-685.

International Search Report and Written Opinion for International Patent Application No. PCT/US2014/029661 mailed Jun. 11, 2014.

International Search Report and Written Opinion for International Patent Application No. PCT/US2014/029664 mailed Jun. 11, 2014.

International Search Report and Written Opinion for International Patent Application No. PCT/US2024/053261 mailed Feb. 6, 2025.

Judge et al., "Potassium Channel Blockers in Multiple Sclerosis: Neuronal Kv Channels and Effects of Symptomatic Treatment," Pharmacology & Therapeutics, 2006, 224-259.

Khadka, P. et al., Pharmaceutical particle technologies: An approach to improve drug solubility, dissolution and bioavailability, Asian Journal of Pharmaceutical Sciences, 9(6): 304-316 (2014).

Kumari A. et al. 3D-QSAR analysis of anilinoquinoline inhibitors of colony stimulating factor-1 kinase(cFMS): implementation of field-based molecular alignment, Med Chem Res 22, 5167-5183 (2013).

Kung et al., "Structure Activity Relationships of Quinoline-Containing c-Met Inhibitors," European Journal of Medicinal Chemistry 43, 2008, 1321-1329.

Kuster et al., "Kinase Inhibitors Methods and Protocols," Methods in Molecular Biology, 2012, 1-46.

Lewitt, "Levodopa for the Treatment of Parkinson's Disease," New England Journal of Medicine, 2008, 359: 2468-2476.

Luo et al., "Principles of Cancer Therapy: Oncogene and Non-oncogene Addiction," Cell, 2009, 36: 823-837.

Minkin, "Bone Acid Phosphatase: Tartrate-Resistant Acid Phosphatase as a Marker of Osteoclast Function," Calcified Tissue International, 1982, 34: 285-290.

Mitchell et al., "Amyotrophic Lateral Sclerosis," The Lancet, 2007, 369: 2031-2041.

National Cancer Institute (http://www.cancer.gov) 2014.

O'Brien et al., "Vascular Cognitive Impairment," The Lancet Neurology, 2003, 2: 89-98.

Ohno et al., "A c-fms tyrosine kinase inhibitor, Ki20227, suppresses osteoclast differentiation and osteolytic bone destruction in a bone metastasis model," Mol Cancer Ther., 2006, 5(11):2634-2643.

PCT/US2019/068311 International Search Report and Written Opinion mailed Jul. 2, 2020.

(56) References Cited

OTHER PUBLICATIONS

PCT/US2024/058998 International Search Report and Written Opinion mailed Jun. 2, 2025, 11 pages.
PCT/US2024/060067 International Search Report and Written Opinion mailed Apr. 10, 2025, 48 pages.
PCT/US2025/027042 International Search Report and Written Opinion mailed Jul. 23, 2025, 12 pages.
Pyonteck et al., "CSF-1R inhibition alters macrophage polarization and blocks glioma progression," Nature Medicine, 2013, 19(10):1264-1274.
Reber et al., "Stem Cell Factor and its Receptor c-Kit as Targets for Inflammatory Diseases," European Journal of Pharmacology, 2006, 533: 327-340.
Roberts et al., "Antiangiogenic and Antitumor Activity of a Selective PDGFR Tyrosine Kinase Inhibitor, CP-673, 451," Cancer Research, 2005, 957-966.
Rubin et al., "KIT activation is a ubiquitous feature of gastrointestinal stromal tumors," Cancer Research, 2001, 61(22):8118-8121.
Shah et al., "Current Approaches in the Treatment of Alzheimer's Disease," Biomedicine & Pharmacotherapy, 2008, 62: 199-207.
Smith, B. D. et al., "Vimseltinib: A Precision CSF1R Therapy for Tenosynovial Giant Cell Tumors and Diseases Promoted by Macrophages", Molecular Cancer Therapeutics, vol. 20, No. 11, (Aug. 25, 2021), pp. 2098-2109, XP093171464.
Tap et al., "Pexidartinib Versus Placebo for Advanced Tenosynovial Giant Cell Tumour (ENLIVEN): a Randomised Phase 3 Trial, " Lancet, 2019, 394: 478-487.
Tap et al., "Structure-Guided Blockade of CSF1R Kinase in Tenosynovial Giant-Cell Tumor," New England Journal of Medicine, 2015, 373(5):428-437.
Tap, W. D. et al., "Efficacy, safety, and patient-reported outcomes of vimseltinib in patients with tenosynovial giant cell tumor: Results from the phase 3 MOTION trial", Journal of Clinical Oncology, vol. 42, No. 16_suppl, (Jun. 1, 2024), pp. 11500-11500, XP093241007.
Tap, W. D. et al., "Motion: A randomized, phase 3, placebo-controlled, double-blind study of vimseltinib (DCC-3014) for the treatment of tenosynovial giant cell tumour", Journal of Clinical Oncology, vol. 40, No. 16_suppl., (Jun. 2, 2022), pages TPS11590-TPS11590, XP093241022.
Wen et al., "Osteosarcoma Cell-Intrinsic Colony Stimulating Factor-1 Receptor Functions to Promote Tumor Cell Metastasis Through JAG1 Signaling," American Journal of Cancer Research, 2017, 7(4): 801-815.
Yasuda et al., "The Stem Cell Factor/C-Kit Receptor Pathway Enhance Proliferation and Invasion of Pancreatic Cancer Cells," Molecular Cancer, 2006, 5(46): 1-10.
U.S. Appl. No. 11/450,850, filed Jun. 9, 2006, US 2008-0299639 A1.
U.S. Appl. No. 11/963,740, filed Dec. 21, 2007, U.S. Pat. No. 8,163,756.
U.S. Appl. No. 12/829,561, filed Jul. 2, 2010, U.S. Pat. No. 8,586,565.
U.S. Appl. No. 11/870,388, filed Oct. 10, 2007, U.S. Pat. No. 7,790,756.
U.S. Appl. No. 11/854,354, filed Sep. 12, 2007, U.S. Pat. No. 8,188,113.
U.S. Appl. No. 12/105,408, filed Apr. 18, 2008, US 2008-0261965 A1.
U.S. Appl. No. 13/590,955, filed Aug. 21, 2012, US 2013-0079362 A1.
U.S. Appl. No. 13/559,170, filed Jul. 26, 2012, US 2012-0322834 A1.
U.S. Appl. No. 14/214,134, filed Mar. 14, 2014, U.S. Pat. No. 9,133,183.
U.S. Appl. No. 13/785,575, filed Mar. 5, 2013, US 2013-0252977 A1.
U.S. Appl. No. 14/383,803, filed Mar. 5, 2013, U.S. Pat. No. 9,187,474.
U.S. Appl. No. 13/491,394, filed Jun. 7, 2012, U.S. Pat. No. 8,461,179.
U.S. Appl. No. 13/801,753, filed Mar. 13, 2013, U.S. Pat. No. 8,940,756.
U.S. Appl. No. 16/387,315, filed Apr. 17, 2019, Re. 48731.
U.S. Appl. No. 14/214,160, filed Mar. 14, 2014, U.S. Pat. No. 9,193,719.
U.S. Appl. No. 14/214,171, filed Mar. 14, 2014, U.S. Pat. No. 9,181,223.
U.S. Appl. No. 14/214,185, filed Mar. 14, 2014, U.S. Pat. No. 9,382,228.
U.S. Appl. No. 14/214,179, filed Mar. 14, 2014, U.S. Pat. No. 9,309,224.
U.S. Appl. No. 14/535,900, filed Nov. 7, 2014, U.S. Pat. No. 9,457,019.
U.S. Appl. No. 17/845,275, filed Jun. 21, 2022, US 2022-0370423 A1.
U.S. Appl. No. 17/845,278, filed Jun. 21, 2022, US 2022-0370424 A1.
U.S. Appl. No. 16/943,821, filed Jul. 30, 2020, U.S. Pat. No. 11,986,463.
U.S. Appl. No. 18/631,891, filed Apr. 10, 2024, US 2024-0415818 A1.
U.S. Appl. No. 16/943,871, filed Jul. 30, 2020, U.S. Pat. No. 12,102,620.
U.S. Appl. No. 18/815,054, filed Aug. 26, 2024, US 2025-0090506 A1.
U.S. Appl. No. 16/725,282, filed Dec. 23, 2019, U.S. Pat. No. 11,103,507.
U.S. Appl. No. 17/358,137, filed Jun. 25, 2021, U.S. Pat. No. 11,679,110.
U.S. Appl. No. 18/140,942, filed Apr. 28, 2023, U.S. Pat. No. 12,285,430.
U.S. Appl. No. 19/079,727, filed Mar. 14, 2025, US 2025-0205237 A1.
U.S. Appl. No. 16/870,384, filed May 8, 2020, U.S. Pat. No. 11,530,206.
U.S. Appl. No. 17/833,272, filed Jun. 6, 2022, U.S. Pat. No. 12,071,432.
U.S. Appl. No. 18/770,318, filed Jul. 11, 2024, US 2025-0084073 A1.
U.S. Appl. No. 16/870,418, filed May 8, 2020, U.S. Pat. No. 11,518,758.
U.S. Appl. No. 17/832,224, filed Jun. 3, 2022, US 2023-0047915 A1.
U.S. Appl. No. 16/902,989, filed Jun. 16, 2020, U.S. Pat. No. 11,590,134.
U.S. Appl. No. 18/152,993, filed Jan. 11, 2023, U.S. Pat. No. 12,377,097.
U.S. Appl. No. 19/235,263, filed Jun. 11, 2025.
U.S. Appl. No. 16/991,644, filed Aug. 12, 2020, US 2023-0277522 A1.
U.S. Appl. No. 17/180,234, filed Feb. 19, 2021, U.S. Pat. No. 11,185,535.
U.S. Appl. No. 17/504,133, filed Oct. 18, 2021, U.S. Pat. No. 11,576,903.
U.S. Appl. No. 18/314,348, filed May 9, 2023, U.S. Pat. No. 11,801,237.
U.S. Appl. No. 18/463,498, filed Sep. 8, 2023, US 2024-0197696 A1.
U.S. Appl. No. 17/028,640, filed Sep. 22, 2020, U.S. Pat. No. 10,966,966.
U.S. Appl. No. 17/180,218, filed Feb. 19, 2021, U.S. Pat. No. 11,266,635.
U.S. Appl. No. 17/583,977, filed Jan. 25, 2022, U.S. Pat. No. 11,426,390.
U.S. Appl. No. 17/583,985, filed Jan. 25, 2022, U.S. Pat. No. 11,344,536.
U.S. Appl. No. 17/727,307, filed Apr. 22, 2022, U.S. Pat. No. 11,534,432.
U.S. Appl. No. 17/735,678, filed May 3, 2022, U.S. Pat. No. 11,529,336.
U.S. Appl. No. 17/735,682, filed May 3, 2022, U.S. Pat. No. 11,576,904.

(56) References Cited

OTHER PUBLICATIONS

U.S. Appl. No. 17/735,862, filed May 3, 2022, U.S. Pat. No. 11,433,056.
U.S. Appl. No. 17/869,108, filed Jul. 20, 2022, U.S. Pat. No. 11,969,414.
U.S. Appl. No. 18/091,743, filed Dec. 30, 2022, U.S. Pat. No. 11,813,251.
U.S. Appl. No. 18/500,549, filed Nov. 2, 2023, U.S. Pat. No. 12,059,410.
U.S. Appl. No. 18/500,650, filed Nov. 2, 2023, U.S. Pat. No. 12,023,325.
U.S. Appl. No. 18/500,730, filed Nov. 2, 2023, U.S. Pat. No. 12,023,327.
U.S. Appl. No. 18/500,792, filed Nov. 2, 2023, U.S. Pat. No. 12,059,411.
U.S. Appl. No. 18/500,686, filed Nov. 2, 2023, U.S. Pat. No. 12,023,326.
U.S. Appl. No. 18/750,014, filed Jun. 21, 2024, U.S. Pat. No. 12,295,944.
U.S. Appl. No. 18/750,032, filed Jun. 21, 2024, U.S. Pat. No. 12,318,373.
U.S. Appl. No. 19/194,583, filed Apr. 30, 2025.
U.S. Appl. No. 17/180,241, filed Feb. 19, 2021, U.S. Pat. No. 11,395,818.
U.S. Appl. No. 17/735,820, filed May 3, 2022, U.S. Pat. No. 11,612,591.
U.S. Appl. No. 18/148,766, filed Dec. 30, 2022, U.S. Pat. No. 11,896,585.
U.S. Appl. No. 18/178,789, filed Mar. 6, 2023, U.S. Pat. No. 11,793,795.
U.S. Appl. No. 18/448,309, filed Aug. 11, 2023, U.S. Pat. No. 11,850,240.
U.S. Appl. No. 18/448,312, filed Aug. 11, 2023, U.S. Pat. No. 11,903,933.
U.S. Appl. No. 18/448,347, filed Aug. 11, 2023, U.S. Pat. No. 11,844,788.
U.S. Appl. No. 18/448,333, filed Aug. 11, 2023, U.S. Pat. No. 11,850,241.
U.S. Appl. No. 18/518,093, filed Nov. 22, 2023, U.S. Pat. No. 12,064,422.
U.S. Appl. No. 18/490,188, filed Oct. 19, 2023, U.S. Pat. No. 11,911,370.
U.S. Appl. No. 18/490,197, filed Oct. 19, 2023, U.S. Pat. No. 11,918,564.
U.S. Appl. No. 18/518,100, filed Nov. 22, 2023, U.S. Pat. No. 11,969,415.
U.S. Appl. No. 18/518,110, filed Nov. 22, 2023, U.S. Pat. No. 12,023,328.
U.S. Appl. No. 18/758,007, filed Jun. 28, 2024, U.S. Pat. No. 12,318,374.
U.S. Appl. No. 18/795,711, filed Aug. 6, 2024, U.S. Pat. No. 12,226,406.
U.S. Appl. No. 18/795,683, filed Aug. 6, 2024, U.S. Pat. No. 12,213,967.
U.S. Appl. No. 18/795,731, filed Aug. 6, 2024, U.S. Pat. No. 12,213,968.
U.S. Appl. No. 19/085,149, filed Mar. 20, 2025.
U.S. Appl. No. 17/528,478, filed Nov. 17, 2021, U.S. Pat. No. 11,912,668.
U.S. Appl. No. 18/408,956, filed Jan. 10, 2024, US 2024-0376058 A1.
U.S. Appl. No. 18/512,447, filed Nov. 17, 2023.
U.S. Appl. No. 17/534,795, filed Nov. 24, 2021, US 2022-0193083 A1.
U.S. Appl. No. 17/534,768, filed Nov. 24, 2021, U.S. Pat. No. 11,801,238.
U.S. Appl. No. 18/073,886, filed Dec. 2, 2022, US 2023-0382915 A1.
U.S. Appl. No. 18/505,396, filed Nov. 9, 2023, US 2024-0122906 A1.
U.S. Appl. No. 18/683,078, filed Feb. 12, 2024, US 2025-0127790 A1.
U.S. Appl. No. 18/078,269, filed Dec. 9, 2022, US 2023-0357179 A1.
U.S. Appl. No. 18/078,271, filed Dec. 9, 2022, U.S. Pat. No. 12,319,655.
U.S. Appl. No. 19/001,282, filed Dec. 24, 2024, US 2025-0250235 A1.
U.S. Appl. No. 18/073,721, filed Dec. 2, 2022, US 2024-0116877 A1.
U.S. Appl. No. 18/456,831, filed Aug. 28, 2023, US 2024-0150368 A1.
U.S. Appl. No. 17/938,353, filed Oct. 6, 2022, U.S. Pat. No. 11,779,572.
U.S. Appl. No. 18/464,519, filed Sep. 11, 2023, US 2024-0261270 A1.
U.S. Appl. No. 18/389,888, filed Dec. 20, 2023, US 2024-0245660 A1.
U.S. Appl. No. 18/985,885, filed Dec. 18, 2024, US 2025-0206729 A1.
U.S. Appl. No. 15/999,530, filed Aug. 17, 2018, U.S. Pat. No. 11,077,113.
U.S. Appl. No. 17/362,763, filed Jun. 29, 2021, U.S. Pat. No. 11,633,403.
U.S. Appl. No. 18/181,046, filed Mar. 9, 2023, US 2024-0050439 A1.
U.S. Appl. No. 15/999,432, filed Aug. 17, 2018, U.S. Pat. No. 11,179,399.
U.S. Appl. No. 17/501,407, filed Oct. 14, 2021, US 2022-0175788 A1.
U.S. Appl. No. 16/638,727, filed Feb. 12, 2020, U.S. Pat. No. 11,498,919.
U.S. Appl. No. 18/045,605, filed Oct. 11, 2022, US 2023-0322772 A1.
U.S. Appl. No. 16/639,895, filed Feb. 18, 2020, U.S. Pat. No. 11,219,618.
U.S. Appl. No. 17/644,486, filed Dec. 15, 2021, US 2022-0218688 A1.
U.S. Appl. No. 16/639,900, filed Feb. 18, 2020, U.S. Pat. No. 11,208,423.
U.S. Appl. No. 17/530,119, filed Nov. 18, 2021, U.S. Pat. No. 11,780,858.
U.S. Appl. No. 18/457,682, filed Aug. 29, 2023.
U.S. Appl. No. 16/639,902, filed Feb. 18, 2020, U.S. Pat. No. 11,560,374.
U.S. Appl. No. 18/084,208, filed Dec. 19, 2022, US 2023-0234949 A1.
U.S. Appl. No. 18/457,825, filed Aug. 29, 2023, US 2024-0180923 A1.
U.S. Appl. No. 18/980,378, filed Dec. 13, 2024, US 2025-0236609 A1.
U.S. Appl. No. 18/971,800, filed Dec. 6, 2024, US 2025-0206720 A1.
U.S. Appl. No. 19/079,010, filed Mar. 13, 2025, US 2025-0243182 A1.
U.S. Appl. No. 18/971,846, filed Dec. 6, 2024, US 2025-0205161 A1.
U.S. Appl. No. 19/079,070, filed Mar. 13, 2025, US 2025-0205236 A1.
U.S. Appl. No. 19/295,254, filed Aug. 8, 2025.
U.S. Appl. No. 19/299,588, filed Aug. 14, 2025.
U.S. Appl. No. 19/079,965, filed Mar. 14, 2025.
U.S. Appl. No. 18/980,426, filed Dec. 13, 2024, US 2025-0195487 A1.
U.S. Appl. No. 17/437,552, filed Sep. 9, 2021, US 2022-0144825 A1.

* cited by examiner

PROCESSES OF MAKING CSF-1R INHIBITORS AND METHODS OF USE THEREOF

CROSS-REFERENCE

This application is a continuation of International Application No. PCT/US2025/027041 filed Apr. 30, 2025, which claims priority to U.S. Provisional Application No. 63/641,022 filed May 1, 2024, the contents of which are incorporated herein by reference.

The present disclosure relates to processes of making a compound represented by Formula (I) or (II) and methods of use thereof.

BACKGROUND

Colony-stimulating factor 1 receptor (CSF-1R) and its ligand, colony stimulating factor 1 (CSF-1) together form a lineage dependency for normal macrophage development and differentiation from monocytes. As such, tumor-associated macrophages (TAMs) are dependent on CSF-1R (also known as FMS) kinase activity for proliferation, and maintenance of their differentiated state and immunosuppressive phenotype. The role of TAMs in promoting an invasive and immunosuppressive tumor microenvironment is well established. TAMs mediate tumor growth, angiogenesis, invasiveness, metastasis, and immunosuppression through the secretion of and response to a variety of cytokines or other soluble factors. TAMs are educated by tumors to enable escape from immune surveillance by dampening a cytotoxic T cell immune response, thereby shielding the tumor from T cell eradication. For example, TAMs express PD-L1, a known immunosuppressive checkpoint that induces T cell anergy.

Several inhibitors targeting CSF-1R have advanced into the clinic as direct antitumor therapies and potential immunotherapies. Many of these drugs also inhibit the closely related Type III receptor tyrosine kinases KIT, PDGFRα/β and FLT3, which may limit their utility due to off-target toxicity. Antibodies targeting CSF-1R are much more specific yet result in >10,000-fold increases in plasma levels of CSF-1, the ligand for CSF-1R, due to blockade of CSF-1 clearance, among other drawbacks.

Tenosynovial giant cell tumor (TGCT) is a proliferative and inflammatory disease that includes entities formerly known as pigmented villonodular synovitis (PVNS), and giant cell tumor of the tendon sheath (GCTTS), intraarticular or extraarticular. It is a rare neoplasm of the joint or tendon sheath, with destructive proliferation of synovial like mononuclear cells, admixed with multinucleate giant cells, foam cells, siderophages and inflammatory cells. There are two types of TGCT: the local or nodular form (where the tumor involves the tendons that support the joint, or in one area of the joint) and the diffuse form (where the entire lining of the joint is involved). Treatment is surgical excision of the tumor. However, it is often difficult to perform a marginal excision for the diffuse form of TGCT resulting in a high recurrence rate. It can be characterized by overexpression of CSF-1.

Thus, there is a need for selective small-molecule CSF-1R inhibitors that are useful in the treatment of disorders associated with the proliferation of TAMs including solid tumors of various cancers and treatment of mesenchymal tumors including TGCT and diffuse-type tenosynovial giant cell tumor (DTGCT).

Certain impurities may be incompatible with other substances in a composition when formulated into pharmaceutical compositions comprising the active pharmaceutical ingredient and a pharmaceutically acceptable carrier; reduce shelf life of the composition; cause difficulties during formulation and use of the composition; cause physical and chemical instabilities of the compositions; lower therapeutic effects of the composition; show adverse biological effects such as genotoxicity; or change the odor, color, or taste of the composition. Therefore, there is a need for a highly pure active pharmaceutical ingredient. Provided herein, in some embodiments, are processes of making a compound represented by Formula (I) that is highly pure and methods of use thereof.

SUMMARY

Described herein, in part, are processes of making a compound represented by Formula (I):

(I)

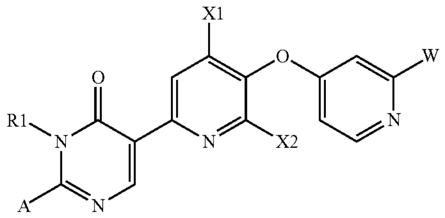

and methods of use thereof.

In some embodiments, provided herein are pharmaceutical compositions comprising a compound of Formula (I), and a pharmaceutically acceptable carrier.

Provided herein, in part, are methods of treating diseases and conditions including, but not limited to a tenosynovial giant cell tumor (TGCT) including diffuse-type tenosynovial giant cell tumor (DTGCT) and localized tenosynovial giant cell tumor. Provided herein, in part, are methods of treating diseases and conditions including, but not limited to graft versus host disease (GVHD) including chronic graft versus host disease (cGVHD) and acute graft versus host disease (aGVHD). Provided herein, in part, are methods of treating diseases and conditions including, but not limited to a neurodegenerative diseases or conditions including Parkinson's disease (PD), Alzheimer's Disease (AD), frontotemporal dementia (FTD), amyotrophic lateral sclerosis (ALS), mild cognitive impairment, and Huntington's Disease (HD). Provided herein, in part, are methods of treating diseases and conditions including, but not limited to, solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, wherein solid tumors include, but are not limited to, ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumors. Provided herein, in part, are methods of treating diseases and conditions including, but not limited to tumors known to have expression of colony-stimulating factor 1 receptor (CSF-1R) or its ligands, colony stimulating factor-1 (CSF-1), or interleukin (IL)-34 (IL-34). Provided herein, in part, are methods of treating diseases and conditions including, but not limited to metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis. Provided herein, in part, are methods of treating diseases and conditions using the compound represented by Formula (I), and pharmaceutical compositions and/or pharmaceutical formulations thereof.

DETAILED DESCRIPTION

The features and other details of the disclosure will now be more particularly described. Certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

Terms used in the singular will also include the plural. For example, "a" means one or more unless indicated otherwise.

All ranges recited herein include the endpoints, including those that recite a range "between" two values. The terms "substantially" and "about" are to be construed as modifying a term or value such that it is not an absolute. This includes, at very least, the degree of expected experimental variance, experimental error, technique variance, technique error and instrument variance, instrumental error for a given technique used to measure a value.

As used herein, "about" includes and describes the value or parameter per se. For example, "about x" includes and describes "x" per se. In some embodiments, the term "about" when used in association with a measurement, or used to modify a value, a unit, a constant, or a range of values, refers to variations of ±10%.

As used herein, the term "adding" does not limit the order, method or how the materials being added are combined, unless indicated otherwise. For instance, "adding X to Y" may also describe "adding Y to X." Furthermore, "adding X and Y to Z" may also describe the various other combinations such as "adding X to Y and Z," "adding X and Z to Y," "adding Y to X and Z," "adding Y and Z to X," and "adding Z to X and Y."

As used herein, the term "excipient" refers to a substance that may be beneficial to include in a composition with an active agent. The term "excipient" includes inert substances as well as functional excipients that may result in beneficial properties of the composition. Exemplary excipients include but are not limited to polymers, glidants, sugars, lubricants, salts, buffers, fats, fillers, disintegrating agents, binders, surfactants, high surface area substrates, flavorants, carriers, matrix materials, diluents, and so forth.

As used herein, the terms "individual," "patient," or "subject" are used interchangeably and include any animal, including mammals, preferably mice, rats, other rodents, rabbits, dogs, cats, swine, cattle, sheep, horses, or primates, and most preferably humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like).

As used herein, the terms "pharmaceutically acceptable" or "pharmacologically acceptable" includes molecular entities and compositions that do not produce an adverse, allergic or other untoward reaction when administered to an animal, or a human, as appropriate. For human administration, preparations should meet sterility, pyrogenicity, and general safety and purity standards as required by FDA standards.

As used herein, the term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

As used herein, the term "pharmaceutical composition" as used herein refers to a composition comprising at least one compound as disclosed herein Formulated together with one or more pharmaceutically acceptable carriers, excipients or diluents.

As used herein, the term "pharmaceutically acceptable salt(s)" refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, the term "therapeutically effective amount" means the amount of the subject compound that will elicit the biological or medical response of a tissue, system or animal, (e.g., mammal or human) that is being sought by the researcher, veterinarian, medical doctor or other clinician. A compound described herein, e.g., the compound represented by Formula (I), is administered in therapeutically effective amounts to treat a condition, e.g., TGCT, GVHD, or neurodegenerative diseases. Alternatively, a therapeutically effective amount of a compound is the quantity required to achieve a desired therapeutic and/or prophylactic effect, such as an amount which results in the prevention of or a decrease in the symptoms associated with the condition.

As used herein and unless otherwise indicated, the terms "treat," "treating" and "treatment" refer to the alleviation of a disease or disorder and/or at least one of its attendant symptoms, and includes any effect, e.g., lessening, reducing, modulating, or eliminating, that results in the improvement of the condition, disease, disorder and the like.

As used herein and unless otherwise indicated, the terms "prevent," "preventing" and "prevention" refer to the inhibition of a symptom of a disease or disorder or the disease itself.

As used herein, the term "active agent" means a drug, medicament, pharmaceutical, therapeutic agent, for example, the compound represented by Formula (I), as described herein.

As used herein, the term "oral formulation," refers to a composition or medium used to administer a compound as disclosed herein (e.g., the compound represented by Formula (I)) to a subject in need thereof by oral administration. Typically, an oral formulation is administered via the mouth, however, "oral formulation" as used herein is intended to cover any substance which is administered to a subject and is absorbed across a membrane, e.g., a mucosal membrane, of the gastrointestinal tract, including, e.g., the mouth, esophagus, stomach, small intestine, large intestine, and colon. In one embodiment, the oral formulation is a solid oral formulation. In one embodiment, the oral formulation is a solid oral formulation administered to a subject in need thereof via the mouth.

A reaction mixture may be characterized herein as being at or allowed to come to "room temperature" or "ambient temperature," often abbreviated as "RT" or "rt." This means that the temperature of the thing is close to, or the same as, that of the space, e.g., the room or fume hood, in which the thing is located. In some embodiments, room temperature is about 20° C. to about 30° C. In some embodiments, room temperature is about 22° C. to about 27° C. In some embodiments, room temperature is 25° C.

The amount of solvent employed in a chemical process, e.g., a reaction, may be referred to herein as a number of "volumes" or "vol" or "V." In this context, this expression would be understood to mean milliliters of the solvent per gram of the material being suspended or dissolved. For example, a material may be referred to as being suspended or dissolved in 10 volumes (or 10 vol or 10V) of a solvent, such that suspending or dissolving 5 grams of a material in 10 volumes of a solvent means that the solvent is used in an amount of 10 milliliters (mL) per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 mL reaction mixture would indicate that 150 mL of solvent X was added.

A process or step may be referred to herein as being carried out "overnight." This refers to a time interval, e.g., for the process or step, that spans the time during the night, when that process or step may not be actively observed. In some embodiments, "overnight" is about 8 hours to about 24 hours. In some embodiments, "overnight" is about 10 hours to about 18 hours. In some embodiments, "overnight" is about 16 hours.

As used herein, the term "reduced pressure" refers to a pressure that is less than atmospheric pressure, i.e., less than about 1013 millibars (1013 mbar). In some embodiments, a reduced pressure is about 10 mbar to about 50 mbar. In some embodiments, a reduced pressure is about 30 mbar to about 50 mbar.

In general, provided herein are intermediates to a compound of Formula (I) or (II) and compound of Formula (I) or (II) that are substantially free of any other substance impurities, unless indicated otherwise. For example, the compound represented by Formula (I) will be substantially free of substance impurities. As used herein, "substantially free" means that the compound (e.g., a compound represented by Formula (I) or (II)) contains about 20% or less, about 10% or less, about 5% or less, about 2% or less, or about 1% or less, of any other compounds such as other substance impurities. Thus, a compound (e.g., a compound represented by Formula (I) or (II)) as substantially free of any compounds such as other substance impurities would be understood to contain greater than 80% (w/w), greater than 90% (w/w), greater than 95% (w/w), greater than 98% (w/w), or greater than 99% (w/w) of the said compound (e.g., a compound represented by Formula (I) or (II)).

As used herein, "substantially free" means that the compound of the present disclosure (e.g., a compound represented by Formula (I) or (II)) contain 20% (w/w) or less of other compounds such as other substance impurities. According to some embodiments, the compounds of the present disclosure contain 10% (w/w) or less, 5% (w/w) or less, 2% (w/w), 1% (w/w) or less of other compounds such as substance impurities.

As used herein, "undetectable" refers to a substance that is present in quantities less than the level of detection of the instrument or systems of detection that are currently commercially available, for example, analytical high-performance liquid chromatography (HPLC), ultra-low dispersion chromatography (ULDC) and ultra-high-performance liquid chromatography (UHPLC) systems.

As used herein, "AUC" refers to the area under the curve in a liquid chromatography analysis disclosed herein. In some embodiments, the liquid chromatography analysis is a high performance liquid chromatography (HPLC) analysis. In some embodiments, the liquid chromatography analysis is an ultra-high performance liquid chromatography (UHPLC) analysis.

As used herein, "area %" or "% area under the curve" refers to the percentage of area under the curve (AUC) of a peak with respect to the total area under the curve of all peaks in a liquid chromatography analysis disclosed herein. The area % or % area under the curve of a peak in a liquid chromatography analysis disclosed herein is a measure of the amount of a compound with respect to the total amount of compounds present in the sample being analyzed. In some embodiments, the liquid chromatography analysis is a high performance liquid chromatography (HPLC) analysis. In some embodiments, the liquid chromatography analysis is an ultra-high-performance liquid chromatography (UHPLC) analysis.

As used herein, "TAM" refers to tumor-associated macrophage.

As used herein, "TGCT" refers to tenosynovial giant cell tumor.

As used herein, "DTGCT" refers to diffuse or diffuse-type tenosynovial giant cell tumor.

As used herein, "GCTTS" refers to giant cell tumor of the tendon sheath.

As used herein, "PVNS" refers to pigmented villonodular synovitis.

As used herein, "GVHD" refers to graft versus host disease.

As used herein, "AD" refers to Alzheimer's Disease.

As used herein, "PD" refers to Parkinson's Disease.

As used herein, "HD" refers to Huntington's Disease.

As used herein, "FTD" refers to frontotemporal dementia.

As used herein, "ALS" refers to amyotrophic lateral sclerosis.

As used herein, the following definitions shall apply unless otherwise indicated. For purposes of this disclosure, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents, positions of substituents and/or variables are permissible only if such combinations result in stable compounds.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the disclosed compounds can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure result.

As used herein, the term "optionally substituted" refers to the replacement of one to six hydrogen atoms in a given structure with the radical of a specified substituent including, but not limited to: hydroxyl, hydroxyalkyl, alkoxy, halogen, alkyl, aryl, cycloalkyl, heterocyclyl, amino, aminoalkyl, cyano, haloalkyl, haloalkoxy, $-OC(=O)-CH_2-$Oalkyl. Preferably, "optionally substituted" refers to the replacement of one to four hydrogen atoms in a given structure with the substituents mentioned above. More preferably, one to three hydrogen atoms are replaced by the substituents as mentioned above. It is understood that the substituent can be further substituted.

As used herein, the term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched, and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms.

Substituents can include any substituents described herein, for example, such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a heteroaralkyl, or an aromatic or heteroaromatic moiety. It will be understood by those skilled in the art that substituents can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), $-CF_3$, $-CN$, and the like. Unless specifically stated as "unsubstituted," references to chemical moieties herein are understood to include substituted variants. For example, reference to an "aryl" group or moiety implicitly includes both substituted and unsubstituted variants.

As used herein, the term "alkyl" refers to a straight chained or branched non-aromatic hydrocarbon which is completely saturated. Typically, a straight chained or branched alkyl group has from 1 to about 20 carbon atoms, preferably from 1 to about 10, e.g., may be $C_1$-$C_{10}$alkyl or e.g., $C_1$-$C_6$alkyl unless otherwise defined. Examples of straight chained and branched alkyl groups include, but are not limited to, methyl, ethyl, 1-propyl (n-propyl), 2-propyl, n-butyl, sec-butyl, tertbutyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. Moreover, the term "alkyl" used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. The "alkyl" group may be optionally substituted.

The term "$C_x$-$C_y$" when used in conjunction with a chemical moiety, such as, acyl, acyloxy, alkyl, alkenyl, alkynyl, or alkoxy is meant to include groups that contain from x to y carbons in the chain. For example, the term "$C_x$-$C_y$" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal.

As used herein, the term "hydrocarbyl" refers to a group that is bonded through a carbon atom that does not have a $=O$ or $=S$ substituent, and typically has at least one carbon-hydrogen bond and a primarily carbon backbone but may optionally include heteroatoms. Thus, groups like methyl, ethoxyethyl, 2-pyridyl, and trifluoromethyl are considered to be hydrocarbyl for the purposes of this application, but substituents such as acetyl (which has a $=O$ substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof. The "hydrocarbyl" group may be optionally substituted.

As used herein, the term "alkoxy" refers to a straight or branched, saturated aliphatic (alkyl) hydrocarbon radical bonded to an oxygen atom that is attached to a core structure. Preferably, alkoxy groups have one to six carbon atoms, i.e., may be C1-C6 alkoxy. Examples of alkoxy groups include but are not limited to methoxy, ethoxy, propoxy, isopropoxy, butoxy, isobutoxy, tert-butoxy, pentoxy, 3-methyl butoxy and the like. The "alkoxy" group may be optionally substituted.

As used herein, the term "haloalkyl" refers to alkyl group (as defined above) is substituted with one or more halogens. A monohaloalkyl radical, for example, may have a chlorine, bromine, iodine, or fluorine atom. Dihalo and polyhaloalkyl radicals may have two or more of the same or different halogen atoms. Examples of haloalkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl, difluoropropyl, and the like. The "haloalkyl" group may be optionally substituted.

As used herein, the term "haloalkoxy" refers to radicals wherein one or more of the hydrogen atoms of the alkoxy group are substituted with one or more halogens. Representative examples of "haloalkoxy" groups include, but not limited to, difluoromethoxy ($—OCHF_2$), trifluoromethoxy ($—OCF_3$), or trifluoroethoxy ($—OCH_2CF_3$). The "haloalkoxy" group may be optionally substituted.

As used herein, the term "aryl" includes substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings (fused rings) wherein at least one of the rings is aromatic. e.g., the other cyclic rings can be cycloalkyls, cycloalkenyls, cycloalkynyls, aryls, heteroaryls, and/or heterocyclyls. The term "fused" means that the second ring is attached or formed by having two adjacent atoms in common with the first ring. The term "fused" is equivalent to the term "condensed". Examples of aryl groups include but are not limited to phenyl, naphthyl, phenanthryl, phenol, aniline, or indanyl and the like. Unless otherwise specified, all aryl groups described herein may be optionally substituted.

As used herein, the terms "polycyclyl", "polycycle", and "polycyclic" refer to two or more rings (e.g., cycloalkyls, cycloalkenyls, cycloalkynyls, aryls, heteroaryls, and/or heterocyclyls) in which one or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

As used herein, the term "cycloalkyl" alone or in combination with other term(s) refers to a cyclic hydrocarbon which is completely saturated. "Cycloalkyl" includes monocyclic, bicyclic, and tricyclic rings. Typically, a monocyclic cycloalkyl group has from 3 to about 10 carbon atoms, more typically 3 to 8 carbon atoms (e.g., $C_3$-$C_{10}$cycloalkyl or e.g., $C_3$-$C_6$cycloalkyl unless otherwise defined. Examples of monocyclic cycloalkyls include cyclopropyl, cyclobutyl, cyclopentyl, cyclohexyl, cycloheptyl and the like. The second ring of a bicyclic cycloalkyl or, the second or third rings of a tricyclic cycloalkyl, may be selected from saturated, unsaturated and aromatic rings. Cycloalkyl includes bicyclic and tricyclic molecules in which one, two or three or more atoms are shared between the two rings. The term "fused cycloalkyl" refers to a bicyclic or tricyclic cycloalkyl in which each of the rings shares two adjacent atoms with the other ring. The second ring of a fused bicyclic cycloalkyl or, the second or third rings of a fused tricyclic cycloalkyl, may be selected from saturated, unsaturated, and aromatic rings. A "cycloalkenyl" group is a cyclic hydrocarbon containing one or more double bonds. Cycloalkyls can be further substituted with alkyls, alkenyls, alkoxys, alkylthios, aminoalkyls, carbonyl-substituted alkyls, $—CF_3$, —CN, and the like. A cycloalkyl may alternatively be polycyclic with more than two rings. Examples of polycyclic cycloalkyls include bridged, fused, and spirocyclic carbocyclyls.

As used herein, the terms "carbocycle," or "carbocyclic" include bicyclic or tricyclic rings in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, 4,5-naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

As used herein, the term "heteroatom" refers an atom of any element other than carbon or hydrogen. Exemplary heteroatoms are nitrogen (N), oxygen (O), sulfur (S), and silicon (Si).

As used herein, the terms "heterocyclyl", "heterocycloalkyl", "heterocycle", and "heterocyclic" refer to a non-aromatic, saturated or partially saturated, including monocyclic, polycyclic (e.g., bicyclic, tricyclic) bridged, or fused, ring system of 3 to 15 member having at least one heteroatom or heterogroup selected from O, N, S, S(O), $S(O)_2$, NH or C(O) with the remaining ring atoms being independently selected from the group consisting of carbon, oxygen, nitrogen, and sulfur. Examples of "heterocyclyl" include, but are not limited to azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, 2-azabicyclo[2.2.2]octanyl, azocinyl, chromanyl, xanthenyl and N-oxides thereof. Attachment of a heterocycloalkyl substituent can occur via either a carbon atom or a heteroatom. A heterocycloalkyl group can be optionally substituted with one or more suitable groups by one or more aforesaid groups. Preferably "heterocyclyl" refers to 5- to 6-membered ring selected from the group consisting of azetidinyl, oxetanyl, imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl, thiomorpholinyl, 1,4-dioxanyl and N-oxides thereof. More preferably, "heterocyclyl" includes azetidinyl, pyrrolidinyl, morpholinyl and piperidinyl. All heterocyclyl are optionally substituted by one or more aforesaid groups.

As used herein, the term "heteroaryl" refers to substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The term "heteroaryl" also refers to substituted or unsubstituted aromatic or partly aromatic ring systems containing at least one heteroatom and having two or more cyclic rings (bicyclic, tricyclic, or polycyclic), containing 8 to 20 ring atoms, suitably 5 to 10 ring atoms, which may be linked covalently, or fused in which two or more atoms are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. The rings may contain an N or S atom, wherein the N or S atom is optionally oxidized, or the N atom is optionally quaternized. All heteroaryls are optionally substituted. Any suitable ring position of the heteroaryl moiety may be covalently linked to a defined chemical structure. Examples of heteroaryl include, but are not limited to: furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, thiadiazolyl, triazolyl, pyridyl, pyrimidinyl, pyrazinyl, pyridazinyl, triazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, alpha-carboline, indolizinyl, benzoisothiazolyl, benzoxazolyl, pyrrolopyridyl, furopyridinyl, purinyl, benzothiadiazolyl, benzoxadiazolyl, benzotriazolyl, benzotriadiazolyl, 7-azaindolyl, 7-azaindazolyl, pyrrolopyridinyl, pyrrolopyrimidinyl, oxazolonepyridinyl, oxazolonepyrimidinyl, imidazolonepyridinyl, imidazolonepyrimidinyl, pyrazolopyridinyl, pyrazolopyrimidinyl, tetrahydronaphthyridinyl, tetrahydropyridolpyriminyl, dihydronaphthyridinonyl, naphthyridinonyl, oxazinanonepyridinyl, oxazinanonepyrimidinyl, carbazolyl, dibenzothienyl, acridinyl and the like.

As used herein, the term "cyano" refers to —CN group.

As used herein, the term "hydroxy" or "hydroxyl" refers to —OH group.

As used herein, the term "halo" or "halogen" alone or in combination with other term(s) means chloro, fluoro, bromo, and iodo.

As used herein, the terms "amine" and "amino" refer to both unsubstituted and substituted amines and salts thereof, e.g., a moiety that can be represented by:

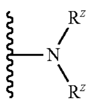 or 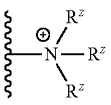

wherein $R^z$ independently represent a hydrogen or optionally substituted hydrocarbyl group, or $R^z$ groups are taken together with the N atom to which they are attached complete a heterocycle having from 4 to 8 atoms in the ring structure which may be optionally substituted.

As used herein, the terms "amide" and "amido" each refer to a group represented by:

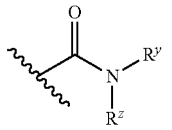 or 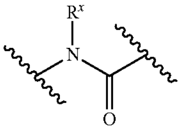

wherein $R^x$, $R^y$, and $R^z$ each independently represents a hydrogen or optionally substituted hydrocarbyl group, or $R^y$ and $R^z$ are taken together with the N atom to which they are attached complete a heterocycle having from 4 to 8 atoms in the ring structure which may be optionally substituted.

As used herein, the terms "urea" refers to a group represented by:

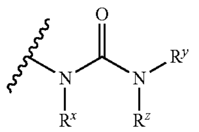

wherein $R^x$, $R^y$, and $R^z$ each independently represents a hydrogen or optionally substituted hydrocarbyl group, or $R^y$ and $R^z$ are taken together with the N atom to which they are attached complete a heterocycle having from 4 to 8 atoms in the ring structure which may be optionally substituted.

The compounds of the disclosure may contain one or more chiral centers and, therefore, exist as stereoisomers. The term "stereoisomers" when used herein consist of all enantiomers or diastereomers. These compounds may be designated by the symbol "R" or "S," depending on the configuration of substituents around the stereogenic carbon atom, but the skilled artisan will recognize that a structure may denote a chiral center implicitly. These compounds may also be designated by "(+)" and "(−)" based on their optical rotation properties. The presently described compounds encompasses various stereoisomers of these compounds and mixtures thereof. Mixtures of enantiomers or diastereomers may be designated by the symbol "(±)" in nomenclature, but the skilled artisan will recognize that a structure may denote a chiral center implicitly.

Individual enantiomers and diastereomers of the disclosed compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations and may involve the use of chiral auxiliaries. For examples, see Carreira and Kvaerno, Classics in Stereoselective Synthesis, Wiley-VCH: Weinheim, 2009.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into the disclosed compounds include isotopes of hydrogen, carbon, nitrogen, oxygen, phosphorus, sulfur, fluorine, and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the disclosure may have one or more H atom replaced with deuterium.

The compound represented by Formula (II) as described herein is also referred to as "vimseltinib." The compound represented by Formula (II) as described herein also refers to 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one.

As used herein, the crystalline dihydrate form of the compound represented by Formula (II) is

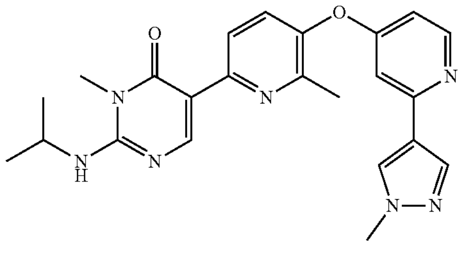

•2 $H_2O$.

The crystalline dihydrate form of the compound represented by Formula (II) is also referred to herein as "vimseltinib dihydrate."

As used herein, IUPAC names were generated using ChemDraw® Professional Version 22.0.0.22.

As used herein, VIII, refers to the compound, 3-((2-chloropyridin-4-yl)oxy)-6-((6-iodo-2-methylpyridin-3-yl)oxy)-2-methylpyridine, the structure of which is the compound of Formula (VIII):

(VIII)

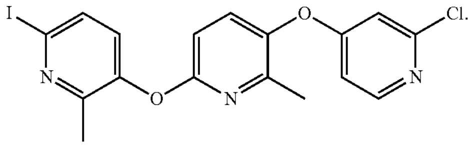

As used herein, XVII, refers to the compound, 3,3'-(pyridine-2,4-diylbis(oxy))bis(6-iodo-2-methylpyridine), the structure of which is the compound of Formula (XVII):

(XVII)

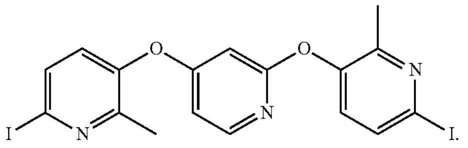

As used herein, XVIII, refers to the compound, 3-((2-chloropyridin-4-yl)oxy)-6-((6-((6-iodo-2-methylpyridin-3-yl)oxy)-2-methylpyridin-3-yl)oxy)-2-methylpyridine, the structure of which is the compound of Formula (XVIII):

(XVIII)

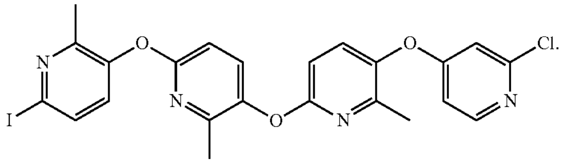

As used herein, XIX, refers to the compound, 3-methyl-5-(6-methyl-5-((2-(methylthio)pyridin-4-yl)oxy)pyridin-2-yl)-2-(methylthio)pyrimidin-4(3H)-one, the structure of which is the compound of Formula (XIX):

(XIX)

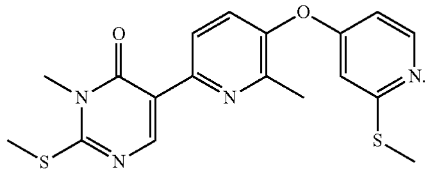

As used herein, XX, refers to the compound, 3-methyl-5-(6-methyl-5-((2-(1-methyl-2-(methylthio)-6-oxo-1,6-dihydropyrimidin-5-yl)pyridin-4-yl)oxy)pyridin-2-yl)-2-(methylthio)pyrimidin-4(3H)-one, the structure of which is the compound of Formula (XX):

(XX)

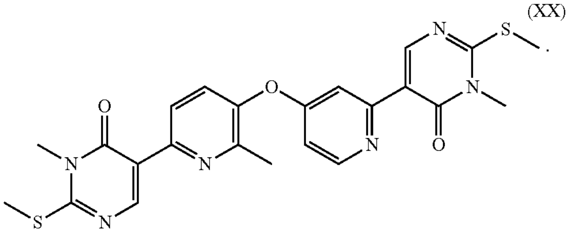

As used herein, XXI, refers to the compound, 3-methyl-2-(1-methyl-1H-pyrazol-4-yl)-5-(6-methyl-5-((2-(1-methyl-1H-pyrazol-4-yl)pyridin-4-yl)oxy)pyridin-2-yl)pyrimidin-4(3H)-one, the structure of which is the compound of Formula (XXI):

(XXI)

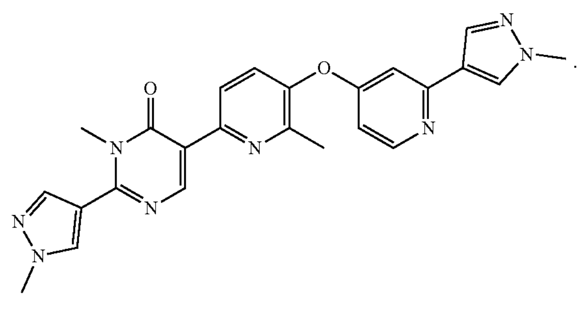

As used herein, XXII, refers to the compound, 2-(isopropylamino)-5-(4-((6-(2-(isopropylamino)-1-methyl-6-oxo-1,6-dihydropyrimidin-5-yl)-2-methylpyridin-3-yl)oxy)pyridin-2-yl)-3-methylpyrimidin-4(3H)-one, the structure of which is the compound of Formula (XXII):

(XXII)

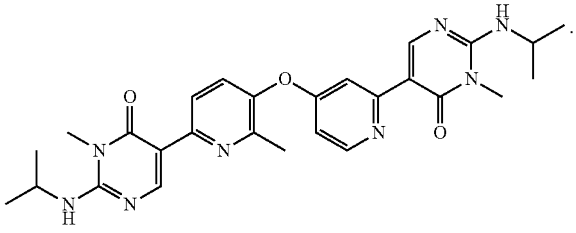

As used herein, XXIII, refers to the compound, 2-(isopropylamino)-3-methyl-5-(6-methyl-5-((2-(methylthio)pyridin-4-yl)oxy)pyridin-2-yl)pyrimidin-4(3H)-one, the structure of which is the compound of Formula (XXIII):

(XXIII)

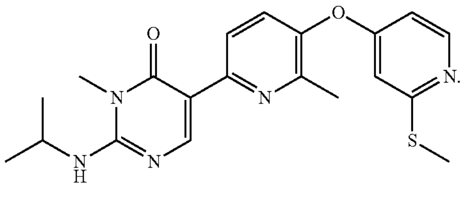

Formula (IX)

In some embodiments, provided herein are processes of preparing a compound of Formula (IX):

(IX)

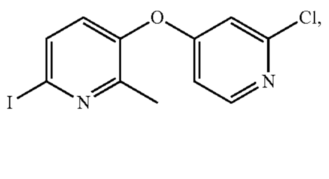

the process comprising reacting a compound of Formula (X):

(X)

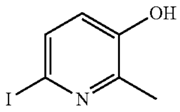

with a compound of Formula (XI):

(XI)

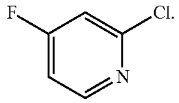

In some embodiments, the process comprises a base. In some embodiment, the base is an organic base. In some embodiments, the base is selected from the group consisting of DBU (1,8-diazabicyclo(5.4.0)undec-7-ene), t-BuOK, (potassium tert-butoxide), 1,5,7-Triazabicyclo(4.4.0)dec-5-ene (TBD), 7-Methyl-1,5,7-triazabicyclo(4.4.0)dec-5-ene (MTBD), and DBN (1,5-diazabicyclo(4.3.0)non-5-ene). In some embodiments, the base is an inorganic base. In some embodiments, the base is selected from the group consisting of $Na_2CO_3$, $K_2CO_3$, and $Cs_2CO_3$. In some embodiments, the base is selected from the group consisting of $K_2CO_3$, $Cs_2CO_3$, DBU (1,8-diazabicyclo(5.4.0)undec-7-ene), t-BuOK, (potassium tert-butoxide), and DBN (1,5-diazabicyclo(4.3.0)non-5-ene). In some embodiments, the base is $K_2CO_3$. At least the aforementioned bases provide the means to perform the reaction.

In some embodiments, the process comprises a solvent. In some embodiments, the solvent is an aprotic solvent. In some embodiments, the solvent is a polar aprotic solvent. In some embodiments, the solvent is a dipolar aprotic solvent. In some embodiments, the solvent is selected from the group consisting of DMSO, DMAc, DMF, NMP, sulfolane, MIBK, acetonitrile, and toluene. In some embodiments, the solvent is selected from the group consisting of DMSO, DMAc, DMF, NMP, sulfolane, MIBK, acetonitrile, and toluene. In some embodiments, the solvent is selected from the group consisting of DMSO, DMAc, NMP, and sulfolane. In some embodiments, the solvent is DMAc. At least the aforementioned solvents provide the means for combining the reaction mixture to perform the reaction.

In some embodiments, the process occurs at a temperature of about 80° C. to about 120° C. In some embodiments, the process occurs at a temperature of about 90° C. to about 120° C. In some embodiments, the process occurs at a temperature of about 100° C. to about 120° C. In some embodiments, the process occurs at a temperature of about 80° C. to about 110° C. In some embodiments, the process occurs at a temperature of about 90° C. to about 110° C. In some embodiments, the process occurs at a temperature of about 100° C. to about 110° C.

In some embodiments, the process occurs at a temperature of about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 108° C., 109° C., 110° C., 111° C., 112° C., 113° C., 114° C., 115° C., 116° C., 117° C., 118° C., 119° C., or 120° C.

In some embodiments, the process occurs at a temperature of about 80° C. In some embodiments, the process occurs at a temperature of about 85° C. In some embodiments, the process occurs at a temperature of about 90° C. In some embodiments, the process occurs at a temperature of about 95° C. In some embodiments, the process occurs at a temperature of about 100° C. In some embodiments, the process occurs at a temperature of about 105° C. In some embodiments, the process occurs at a temperature of about 110° C. In some embodiments, the process occurs at a temperature of about 115° C. In some embodiments, the process occurs at a temperature of about 120° C. At least the aforementioned temperatures provide the means for heating the reaction mixture to perform the reaction. At least the aforementioned bases, solvents, and temperatures provide the means for performing the reaction.

In some embodiments, provided herein is a compound of Formula (IX):

(IX)

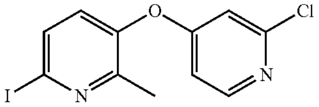

prepared by any one of the processes described herein.

In some embodiments, the compound of Formula (IX), when prepared by a process described herein, is obtained in a composition comprising the compound of Formula (IX) and a compound of Formula (XIII):

(XIII)

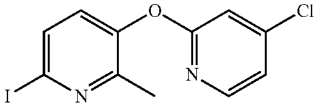

wherein the amount of the compound of Formula (XIII) present in the composition is characterized by an area under the curve of less than about 20% when measured by HPLC.

In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 19% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 18% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 17% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 16% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 15% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 14% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 13% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 12% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 11% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 10% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 9% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 8% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 7% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 6% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 5% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 4% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 3% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 2% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 1% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.5% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.4% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.3% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.2% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.1% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.05% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.04% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.03% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.02% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.015% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is characterized by an area under the curve of less than about 0.01% when measured by HPLC. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is undetectable.

In some embodiments, the compound of Formula (IX), when prepared by a process described herein, is obtained in a composition comprising the compound of Formula (IX) and a compound of Formula (XIII):

(XIII)

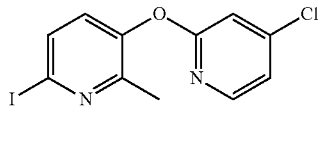

wherein the amount of the compound of Formula (XIII) present in the composition is no more than about 20% weight/weight of the composition.

In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 19% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 18% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 17% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 16% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 15% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 14% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 13% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 12% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 110% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 10% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 9% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 8% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 7% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 6% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 5% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 4% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 3% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 2% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 1% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.5% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.4% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.3% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.2% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.1% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.05% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.04% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.03% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.02% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.015% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is no more than about 0.01% weight/weight of the composition. In some embodiments, the compound of Formula (IX), when prepared by a process described herein, is obtained in a composition comprising the compound of Formula (IX) and a compound of Formula (XIII) wherein the amount of the compound of Formula (XIII) present in the composition is undetectable.

Also provided herein, in some embodiments, is a compound of Formula (IX):

(IX)

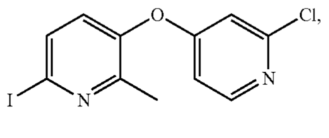

having an undetectable amount to no more than about 20% area under the curve when measured by HPLC of a compound of Formula (XIII):

(XIII)

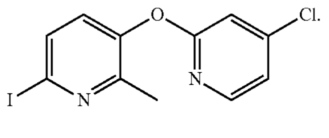

In some embodiments, the compound of Formula (IX) is characterized as having an undetectable amount to no more than about 15% area under the curve when measured by HPLC of a compound of Formula (XIII). In some embodiments, the compound of Formula (IX) is characterized as having an undetectable amount to no more than about 10% area under the curve when measured by HPLC of a compound of Formula (XIII). In some embodiments, the compound of Formula (IX) is characterized as having an undetectable amount to no more than about 5% area under the curve when measured by HPLC of a compound of Formula (XIII). In some embodiments, the compound of Formula (IX) is characterized as having an undetectable amount to no more than about 4% area under the curve when measured by HPLC of a compound of Formula (XIII). In some embodiments, the compound of Formula (IX) is characterized as having an undetectable amount to no more than about 3% area under the curve when measured by HPLC of a compound of Formula (XIII). In some embodiments, the compound of Formula (IX) is characterized as having an undetectable amount to no more than about 2% area under the curve when measured by HPLC of a compound of Formula (XIII). In some embodiments, the compound of Formula (IX) is characterized as having an undetectable amount to no more than about 1% area under the curve when measured by HPLC of a compound of Formula (XIII). In some embodiments, the compound of Formula (IX) is characterized as having an undetectable amount to no more than about 0.5% area under the curve when measured by HPLC of a compound of Formula (XIII). In some embodiments, the compound of Formula (IX) is characterized as having an undetectable amount to no more than about 0.4% area under the curve when measured by HPLC of a compound of Formula (XIII). In some embodiments, the compound of Formula (IX) is characterized as having an undetectable amount to no more than about 0.3% area under the curve when measured by HPLC of a compound of Formula (XIII). In some embodiments, the compound of Formula (IX) is characterized as having an undetectable amount to no more than about 0.2% area under the curve when measured by HPLC of a compound of Formula (XIII). In some embodiments, the compound of Formula (IX) is characterized as having an undetectable amount to no more than about 0.1% area under the curve when measured by HPLC of a compound of Formula (XIII). In some embodiments, the compound of Formula (IX) is characterized as having an undetectable amount to no more than about 0.05% area under the curve when measured by HPLC of a compound of Formula (XIII). In some embodiments, the compound of Formula (IX) is characterized as having an undetectable amount to no more than about 0.04% area under the curve when measured by HPLC of a compound of Formula (XIII). In some embodiments, the compound of Formula (IX) is characterized as having an undetectable amount to no more than about 0.03% area under the curve when measured by HPLC of a compound of Formula (XIII). In some embodiments, the compound of Formula (IX) is characterized as having an undetectable amount to no more than about 0.02% area under the curve when measured by HPLC of a compound of Formula (XIII). In some embodiments, the compound of Formula (IX) is characterized as having an undetectable amount to no more than about 0.015% area under the curve when measured by HPLC of a compound of Formula (XIII). In some embodiments, the compound of Formula (IX) is characterized as having an undetectable amount to no more than about 0.01% area under the curve when measured by HPLC of a compound of Formula (XIII). In some embodiments, the compound of Formula (IX), when prepared by a process described herein, is obtained in a composition comprising the compound of Formula (IX) and a compound of Formula (XIII) wherein the amount of the compound of Formula (XIII) present in the composition is undetectable.

Also provided herein, in some embodiments, are compositions, comprising a compound of Formula (IX):

(IX)

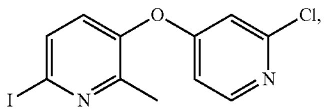

having a purity of greater than or equal to about 99.8% area under the curve when measured by HPLC, and a compound of Formula (XIII), wherein the compound of Formula (XIII) is present in the composition at no more than about 0.2% area under the curve when measured by HPLC.

In some embodiments, the compound of Formula (XIII) is present in the composition at no more than about 0.15% area under the curve when measured by HPLC. In some embodiments, the compound of Formula (XIII) is present in the composition at no more than about 0.1% area under the curve when measured by HPLC. In some embodiments, the compound of Formula (XIII) is present in the composition at no more than about 0.05% area under the curve when measured by HPLC. In some embodiments, the compound of Formula (XIII) is present in the composition at no more than about 0.04% area under the curve when measured by HPLC. In some embodiments, the compound of Formula (XIII) is present in the composition at no more than about 0.03% area under the curve when measured by HPLC. In some embodiments, the compound of Formula (XIII) is present in the composition at no more than about 0.02% area under the curve when measured by HPLC. In some embodiments, the compound of Formula (XIII) is present in the composition at no more than about 0.015% area under the curve when measured by HPLC. In some embodiments, the compound of Formula (XIII) is present in the composition at no more than about 0.01% area under the curve when measured by HPLC.

Formula (IX')

Also provided herein, in some embodiments, are processes of preparing a compound of Formula (IX'):

(IX')

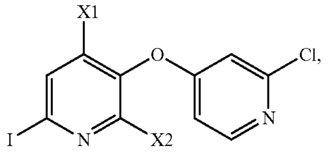

wherein X1 and X2 are each independently selected from the group consisting of H and alkyl, the process comprising reacting a compound of Formula (X'):

(X')

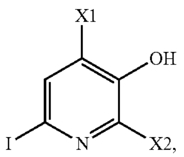

wherein X1 and X2 are as defined above for the compound of Formula (IX'), with a compound of Formula (XI):

(XI)

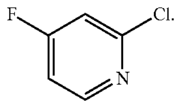

In some embodiments, the process comprises a base. In some embodiment, the base is an organic base. In some embodiments, the base is selected from the group consisting of DBU (1,8-diazabicyclo(5.4.0)undec-7-ene), t-BuOK, (potassium tert-butoxide), 1,5,7-Triazabicyclo(4.4.0)dec-5-ene (TBD), 7-Methyl-1,5,7-triazabicyclo(4.4.0)dec-5-ene (MTBD), and DBN (1,5-diazabicyclo(4.3.0)non-5-ene). In some embodiments, the base is an inorganic base. In some embodiments, the base is selected from the group consisting of $Na_2CO_3$, $K_2CO_3$, and $Cs_2CO_3$. In some embodiments, the base is selected from the group consisting of $K_2CO_3$, $Cs_2CO_3$, DBU (1,8-diazabicyclo(5.4.0)undec-7-ene), t-BuOK, (potassium tert-butoxide), and DBN (1,5-diazabicyclo(4.3.0)non-5-ene). In some embodiments, the base is $K_2CO_3$. At least the aforementioned bases provide the means to perform the reaction.

In some embodiments, the process comprises a solvent. In some embodiments, the solvent is an aprotic solvent. In some embodiments, the solvent is a polar aprotic solvent. In some embodiments, the solvent is a dipolar aprotic solvent. In some embodiments, the solvent is selected from the group consisting of DMSO, DMAc, DMF, NMP, sulfolane, MIBK, acetonitrile, and toluene. In some embodiments, the solvent is selected from the group consisting of DMSO, DMAc, DMF, NMP, sulfolane, MIBK, acetonitrile, and toluene. In some embodiments, the solvent is selected from the group consisting of DMSO, DMAc, NMP, and sulfolane. In some embodiments, the solvent is DMAc. At least the aforementioned solvents provide the means for combining the reaction mixture to perform the reaction.

In some embodiments, the process occurs at a temperature of about 80° C. to about 120° C. In some embodiments, the process occurs at a temperature of about 90° C. to about 120° C. In some embodiments, the process occurs at a temperature of about 100° C. to about 120° C. In some embodiments, the process occurs at a temperature of about 80° C. to about 110° C. In some embodiments, the process occurs at a temperature of about 90° C. to about 110° C. In some embodiments, the process occurs at a temperature of about 100° C. to about 110° C.

In some embodiments, the process occurs at a temperature of about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 109°

C., 110° C., 111° C., 112° C., 113° C., 114° C., 115° C., 116° C., 117° C., 118° C., 119° C., or 120° C.

In some embodiments, the process occurs at a temperature of about 80° C. In some embodiments, the process occurs at a temperature of about 85° C. In some embodiments, the process occurs at a temperature of about 90° C. In some embodiments, the process occurs at a temperature of about 95° C. In some embodiments, the process occurs at a temperature of about 100° C. In some embodiments, the process occurs at a temperature of about 105° C. In some embodiments, the process occurs at a temperature of about 110° C. In some embodiments, the process occurs at a temperature of about 115° C. In some embodiments, the process occurs at a temperature of about 120° C. At least the aforementioned temperatures provide the means for heating the reaction mixture to perform the reaction. At least the aforementioned bases, solvents, and temperatures provide the means for performing the reaction.

In some embodiments, provided herein is a compound of Formula (IX'):

(IX')

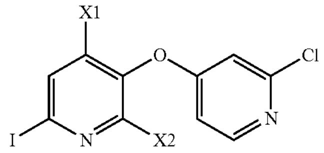

prepared by any one of the processes described herein, wherein X1 and X2 are each independently selected from the group consisting of H and alkyl.

In some embodiments, X1 and X2 are each independently selected from the group consisting of H and $C_1$-$C_6$ alkyl. In some embodiments, X1 and X2 are each independently selected from the group consisting of H and methyl. In some embodiment, X1 is H and X2 is methyl.

In some embodiments, the compound of Formula (IX'), when prepared by a process described herein, is obtained in a composition comprising the compound of Formula (IX') and a compound of Formula (XIII'):

(XIII')

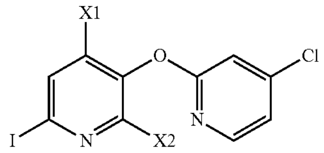

wherein X1 and X2 are as defined for the compound of Formula (IX'), wherein the amount of the compound of Formula (XIII') present in the composition is characterized by an area under the curve of less than about 20% when measured by HPLC.

In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 15% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 10% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 5% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 4% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 3% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 2% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 1% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.5% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.4% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.3% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.2% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.1% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.05% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.04% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.03% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.02% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.015% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is characterized by an area under the curve of less than about 0.01% when measured by HPLC. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is undetectable.

In some embodiments, the compound of Formula (IX'), when prepared by a process described herein, is obtained in a composition comprising the compound of Formula (IX') and a compound of Formula (XIII'):

(XIII')

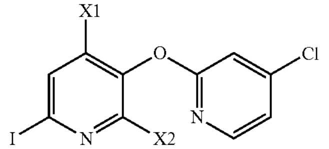

wherein X1 and X2 are as defined for the compound of Formula (IX'), wherein the amount of the compound of Formula (XIII') present in the composition is no more than about 20% weight/weight of the composition.

In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 19% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 18% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 17% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 16% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 15% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 14% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 13% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 12% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 110% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 10% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 9% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 8% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 7% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 6% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 5% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 4% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 3% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 2% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 1% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.5% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.4% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.3% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.2% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.1% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.05% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.04% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.03% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.02% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.015% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is no more than about 0.01% weight/weight of the composition. In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is undetectable.

Also provided herein, in some embodiments, is a compound of Formula (IX'):

(IX')

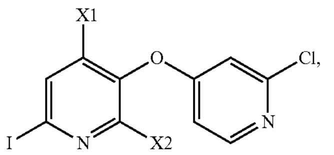

having an undetectable amount to no more than about 20% area under the curve when measured by HPLC of a compound of Formula (XIII'):

(XIII')

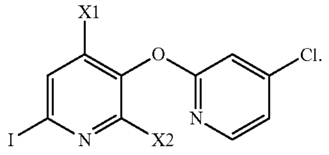

In some embodiments, the compound of Formula (IX') is characterized as having an undetectable amount to no more than about 15% area under the curve when measured by HPLC of a compound of Formula (XIII'). In some embodiments, the compound of Formula (IX') is characterized as having an undetectable amount to no more than about 10% area under the curve when measured by HPLC of a compound of Formula (XIII'). In some embodiments, the compound of Formula (IX') is characterized as having an undetectable amount to no more than about 5% area under the curve when measured by HPLC of a compound of Formula (XIII'). In some embodiments, the compound of Formula (IX') is characterized as having an undetectable amount to no more than about 4% area under the curve when measured by HPLC of a compound of Formula (XIII'). In some embodiments, the compound of Formula (IX') is characterized as having an undetectable amount to no more than about 3% area under the curve when measured by HPLC of a compound of Formula (XIII'). In some embodiments, the compound of Formula (IX') is characterized as having an undetectable amount to no more than about 2% area under the curve when measured by HPLC of a compound of Formula (XIII'). In some embodiments, the compound of Formula (IX') is characterized as having an undetectable amount to no more than about 1% area under the curve when measured by HPLC of a compound of Formula (XIII'). In some embodiments, the compound of Formula (IX') is characterized as having an undetectable amount to no more than about 0.5% area under the curve when measured by HPLC of a compound of Formula (XIII'). In some embodiments, the compound of Formula (IX') is characterized as having an undetectable amount to no more than about 0.4% area under the curve when measured by HPLC of a compound of Formula (XIII'). In some embodiments, the compound of Formula (IX') is characterized as having an undetectable amount to no more than about 0.3% area under the curve when measured by HPLC of a compound of Formula (XIII'). In some embodiments, the compound of Formula (IX') is characterized as having an undetectable amount to no more than about 0.2% area under the curve when measured by HPLC of a compound of Formula (XIII'). In some embodiments, the compound of Formula (IX') is characterized as having an undetectable amount to no more than about 0.1% area under the curve when measured by HPLC of a compound of Formula (XIII'). In some embodiments, the compound of Formula (IX') is characterized as having an undetectable amount to no more than about 0.05% area under the curve when measured by HPLC of a compound of Formula (XIII'). In some embodiments, the compound of Formula (IX') is characterized as having an undetectable amount to no more than about 0.04% area under the curve when measured by HPLC of a compound of Formula (XIII'). In some embodiments, the compound of Formula (IX') is characterized as having an undetectable amount to no more than about 0.03% area under the curve when measured by HPLC of a compound of Formula (XIII'). In some embodiments, the compound of Formula (IX') is characterized as having an undetectable amount to no more than about 0.02% area under the curve when measured by HPLC of a compound of Formula (XIII'). In some embodiments, the compound of Formula (IX') is characterized as having an undetectable amount to no more than about 0.015% area under the curve when measured by HPLC of a compound of Formula (XIII'). In some embodiments, the compound of Formula (IX') is characterized as having an undetectable amount to no more than about 0.01% area under the curve when measured by HPLC of a compound of Formula (XIII'). In some embodiments, the compound of Formula (IX'), when prepared by a process described herein, is obtained in a composition comprising the compound of Formula (IX') and a compound of Formula (XIII') wherein the amount of the compound of Formula (XIII') present in the composition is undetectable.

Also provided herein, in some embodiments, are compositions, comprising a compound of Formula (IX'):

(IX')

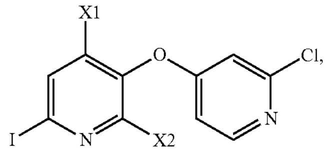

having a purity of greater than or equal to about 99.8% area under the curve when measured by HPLC, and a compound of Formula (XIII'), wherein the compound of Formula (XIII') is present in the composition at no more than about 0.2% area under the curve when measured by HPLC.

In some embodiments, the compound of Formula (XIII') is present in the composition at no more than about 0.15% area under the curve when measured by HPLC. In some embodiments, the compound of Formula (XIII') is present in the composition at no more than about 0.1% area under the curve when measured by HPLC. In some embodiments, the compound of Formula (XIII') is present in the composition at no more than about 0.05% area under the curve when measured by HPLC. In some embodiments, the compound of Formula (XIII') is present in the composition at no more than about 0.04% area under the curve when measured by HPLC. In some embodiments, the compound of Formula (XIII') is present in the composition at no more than about 0.03% area under the curve when measured by HPLC. In some embodiments, the compound of Formula (XIII') is present in the composition at no more than about 0.02% area under the curve when measured by HPLC. In some embodiments, the compound of Formula (XIII') is present in the composition at no more than about 0.015% area under the curve when measured by HPLC. In some embodiments, the compound of Formula (XIII') is present in the composition at no more than about 0.01% area under the curve when measured by HPLC.

Formula (I)

In some embodiments, provided herein are processes of preparing a compound of Formula (I):

(I)

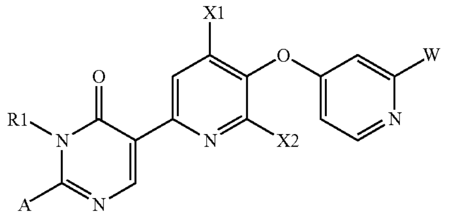

or a pharmaceutically acceptable salt, hydrate, enantiomer, stereoisomer, or tautomer thereof, wherein A is selected from the group consisting of amino, cycloalkyl, and heterocyclyl;

W is selected from the group consisting of heteroaryl, aryl, amido and urea;

X1 and X2 are each independently selected from the group consisting of H and alkyl; and R1 is selected from the group consisting of H and alkyl;

the process comprising:

reacting a compound of Formula (IX'):

(IX')

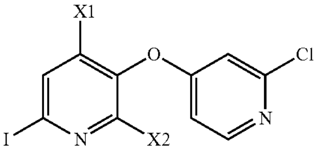

wherein the compound of Formula (IX') is optionally prepared by a process described herein, wherein X1 and X2 are as defined as above for the compound of Formula (I), with a compound of Formula (XII'):

(XII')

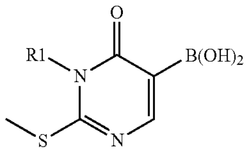

wherein R1 is as defined as above for the compound of Formula (I), in the presence of a first catalyst to produce a compound of Formula (IV'):

(IV')

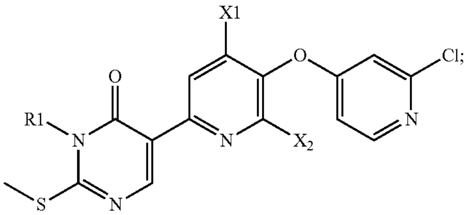

reacting the compound of Formula (IV') with a compound represented by M-W, wherein M is selected from the group consisting of H, trialkylstannyl, a boronic acid, and a boronate ester, and W is as defined as above for the compound of Formula (I), provided that, when M is H, then W is selected from the group consisting of amido and urea, in the presence of a second catalyst, to produce a compound of Formula (III'):

(III')

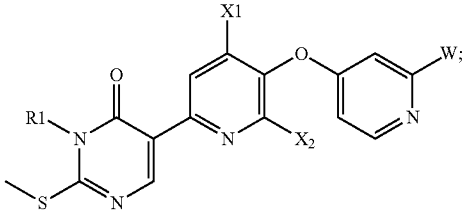

reacting the compound of Formula (III') with a compound represented by A-H, wherein A is as defined as above for the compound of Formula (I), thereby preparing the compound of Formula (I).

In some embodiments, A is 4-10 membered heterocyclyl containing at last one ring N atom and optionally one additional ring O, S, or N atom. In some embodiments, A is 4-8 membered heterocyclyl containing at last one ring N atom and optionally one additional ring O, S, or N atom. In some embodiments, A is 4-6 membered heterocyclyl containing at last one ring N atom and optionally one additional ring O, S, or N atom. In some embodiments, A is selected from the group consisting of amino,

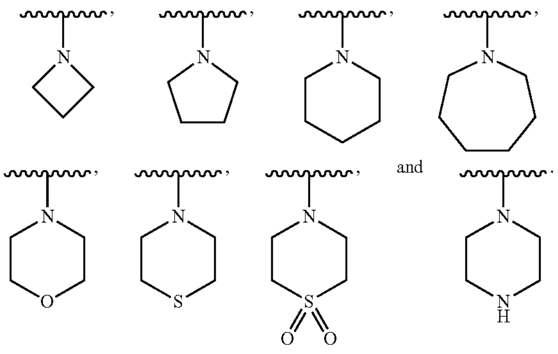

and

In some embodiments, A is amino. In some embodiments, A is N(R11)(R12), wherein R11 and R12 are each independently H or alkyl. In some embodiments, R11 is H. In some embodiments, R11 is $C_{1-6}$alkyl. In some embodiments, R12 is H. In some embodiments, R12 is $C_{1-6}$alkyl. In some embodiments, A is NH—$CH(CH_3)_2$.

In some embodiments, W is a 5-10 membered heteroaryl. In some embodiments, W is a 5-6 membered heteroaryl. In some embodiments, W is a 5-membered heteroaryl.

In some embodiments, W is a 5-10 membered heteroaryl substituted with H, alkyl, cycloalkyl, or heterocyclyl. In some embodiments, W is a 5-6 membered heteroaryl substituted with H, alkyl, cycloalkyl, or heterocyclyl. In some embodiments, W is a 5-membered heteroaryl substituted with H, alkyl, cycloalkyl, or heterocyclyl.

In some embodiments, W is

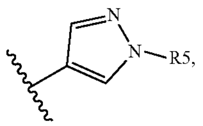

and R5 is selected from the group consisting of H, alkyl, cycloalkyl, and heterocyclyl.

In some embodiments, R5 is alkyl. In some embodiments, R5 is $C_1$-$C_6$ alkyl. In some embodiments, R5 is $CH_3$. In some embodiments, W is

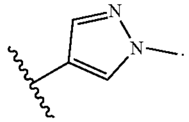 [SMILES: *c1cnn(C)c1]

In some embodiments, X1 and X2 are each independently selected from the group consisting of H and $C_1$-$C_6$ alkyl. In some embodiments, one of X1 and X2 is alkyl and the other is H. In some embodiments, one of X1 and X2 is $C_1$-$C_6$ alkyl and the other is H. In some embodiments, X1 is H and X2 is $CH_3$.

In some embodiments, R1 is alkyl. In some embodiments, R1 is $C_1$-$C_6$ alkyl. In some embodiments, R1 is $CH_3$.

In some embodiments, the first catalyst is a palladium catalyst. In some embodiments, the first catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$. In some embodiments, the first catalyst is $Pd(PPh_3)_4$.

In some embodiments, the second catalyst is a palladium catalyst. In some embodiments, the second catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$. In some embodiments, the second catalyst is $Pd(PPh_3)_4$.

In some embodiments, the compound of Formula (I) is a compound of Formula (Ia):

(Ia)

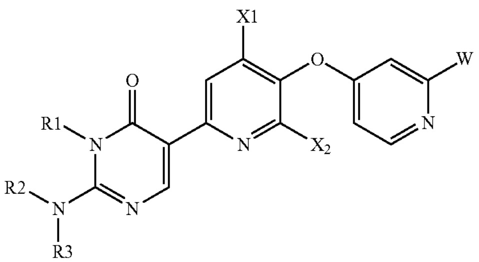

or a pharmaceutically acceptable salt, hydrate, enantiomer, stereoisomer, or tautomer thereof, wherein R2 and R3 are each independently selected from the group consisting of H and alkyl.

In some embodiments, R3 is H.

In some embodiments, R2 is alkyl.

In some embodiments, the compound of Formula (Ia) is a compound of Formula (Ib):

(Ib)

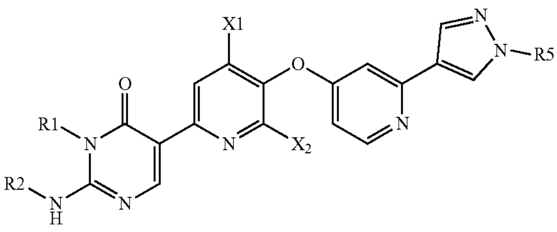

or a pharmaceutically acceptable salt, hydrate, enantiomer, stereoisomer, or tautomer thereof.

In some embodiments, one of X1 and X2 is alkyl and the other is H.

In some embodiments, R1 is alkyl. In some embodiments, R1 is $CH_3$.

In some embodiments, R2 is alkyl.

In some embodiments, the compound of Formula (I) is a compound of Formula (Ic):

(Ic)

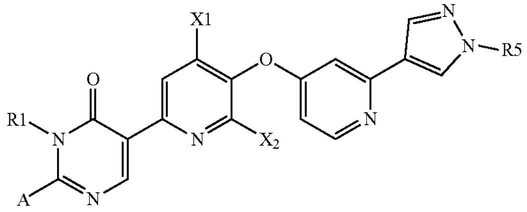

or a pharmaceutically acceptable salt, hydrate, enantiomer, stereoisomer, or tautomer thereof.

In some embodiments, one of X1 and X2 is alkyl and the other is H.

In some embodiments R1 is alkyl. In some embodiments, R1 is $CH_3$.

In some embodiments, A is amino. In some embodiments, A is NH—$CH(CH_3)_2$. In some embodiments, the compound of formula (I) is (II)

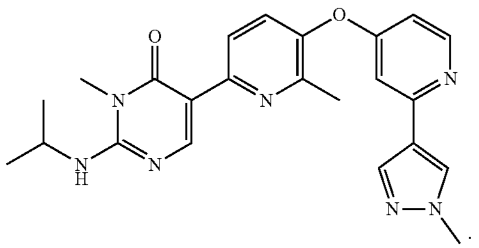

In some embodiments, provided herein is a compound of Formula (I), or a pharmaceutically acceptable salt, hydrate, enantiomer, stereoisomer, or tautomer thereof, prepared by a process described herein.

In some embodiments, the compound of Formula (I), when prepared by a process disclosed herein, is present in the pharmaceutically acceptable formulation as a hydrate form (the compound of Formula (I)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (I) is present in a composition or a pharmaceutically acceptable formulation as a dihydrate form.

In some embodiments, the compound of Formula (I), when prepared by a process described herein, is obtained in a composition comprising the compound of Formula (I) and a compound of Formula (XIV'):

(XIV')

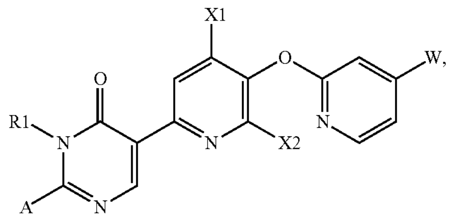

wherein the amount of the compound of Formula (XIV') present in the composition is undetectable or is no more than about 5% weight/weight of the composition.

In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 4.5% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 4% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 3.5% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 3% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 2.5% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 2% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 1.5% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 1% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.9% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.8% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.7% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.6% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.5% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.4% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.3% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.2% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.15% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.1% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.09% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.08% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.07% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.06% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.05% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.04% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.05% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.03% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.02% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.015% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable or is no more than about 0.01% weight/weight of the composition. In some embodiments, the compound of Formula (I), when prepared by a process described herein, is obtained in a composition comprising the compound of Formula (I) and a compound of Formula (XIV') wherein the amount of the compound of Formula (XIV') present in the composition is undetectable.

In some embodiments, provided herein is a compound of Formula (I):

(I)

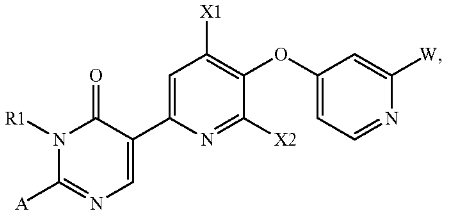

or a pharmaceutically acceptable salt, hydrate, enantiomer, stereoisomer, or tautomer thereof, having an undetectable amount to no more than about 5% area under the curve when measured by HPLC of a compound of Formula (XIV'):

(XIV')

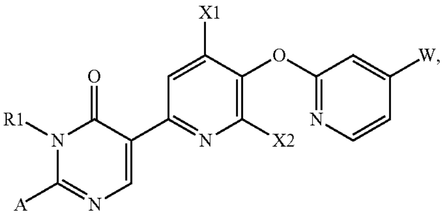

wherein X1, X2, W, A, and R1 are as defined herein for the compound of Formula (I).

In some embodiments, the compound of Formula (I), or a pharmaceutically acceptable salt, hydrate, enantiomer, stereoisomer, or tautomer thereof, is characterized as having an undetectable amount to no more than about 4.5% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 4% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 3.5% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 3% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 2.5% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 2% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 1.5% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 1% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.5% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.4% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.3% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.2% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.15% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.1% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.09% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.08% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.07% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.06% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.05% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.04% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.03% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.02% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.015% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount to no more than about 0.01% area under the curve when measured by HPLC of a compound of Formula (XIV'). In some embodiments, the compound of Formula (I), or a pharmaceutically acceptable salt, hydrate, enantiomer, stereoisomer, or tautomer thereof, is characterized as having an undetectable amount a compound of Formula (XIV').

In some embodiments, provided herein are compositions, comprising a compound of Formula (I):

(I)

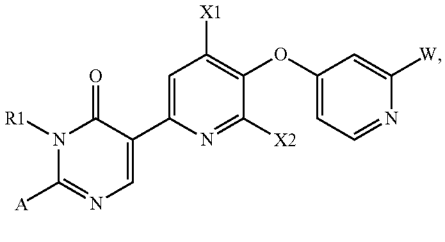

or a pharmaceutically acceptable salt, hydrate, enantiomer, stereoisomer, or tautomer thereof, having a purity of greater than or equal to about 99.8% area under the curve when measured by HPLC, and a compound of Formula (XIV'):

(XIV')

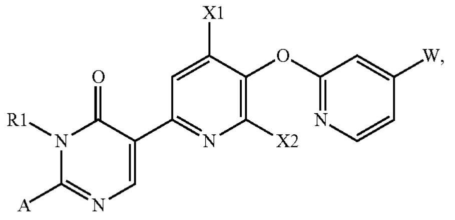

or a pharmaceutically acceptable salt, hydrate, enantiomer, stereoisomer, or tautomer thereof, wherein the compound of Formula (XIV') is present in the composition at no more than about 0.2% area under the curve when measured by HPLC.

In some embodiments, the compound of Formula (XIV') is present in the composition at no more than about 0.15% area under the curve when measured by HPLC. In some embodiments, the compound of Formula (XIV') is present in the composition at no more than about 0.1% area under the curve when measured by HPLC. In some embodiments, the compound of Formula (XIV') is present in the composition at no more than about 0.05% area under the curve when measured by HPLC. In some embodiments, the compound of Formula (XIV') is present in the composition at no more than about 0.04% area under the curve when measured by HPLC. In some embodiments, the compound of Formula (XIV') is present in the composition at no more than about 0.03% area under the curve when measured by HPLC. In some embodiments, the compound of Formula (XIV') is present in the composition at no more than about 0.02% area under the curve when measured by HPLC. In some embodiments, the compound of Formula (XIV') is present in the composition at no more than about 0.015% area under the curve when measured by HPLC. In some embodiments, the compound of Formula (XIV') is present in the composition at no more than about 0.01% area under the curve when measured by HPLC.

Formula (II)

In some embodiments, provided herein are processes of preparing a compound of Formula (II):

(II)

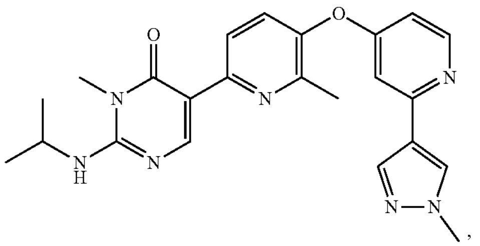

the process comprising:

reacting a compound of Formula (IX):

(IX)

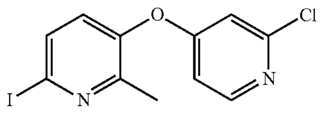

wherein the compound of Formula (IX) is optionally prepared by a process described herein, with a compound of Formula (XII):

(XII)

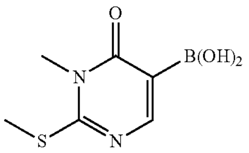

in the presence of a first catalyst to produce a compound of Formula (IV):

(IV)

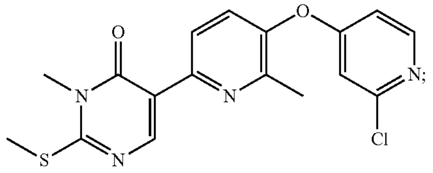

reacting the compound of Formula (IV) with a compound represented by:

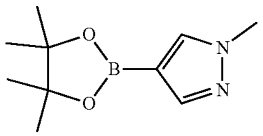

in the presence of a second catalyst, to produce a compound of Formula (III):

(III)

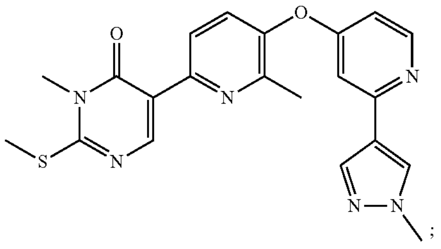

and reacting the compound of Formula (III) with isopropylamine, thereby preparing the compound of Formula (II).

In some embodiments, the first catalyst is a palladium catalyst. In some embodiments, the first catalyst is selected from the group consisting of $Pd(PPh_3)_4$, $Pd(OAc)_2$/SPhos, Pd(dppf)$Cl_2$, Pd(dppf)$Cl_2$·DCM, XPhos Pd G2, and $Pd_2(dba)_3$. In some embodiments, the first catalyst is $Pd(PPh_3)_4$.

In some embodiments, the second catalyst is a palladium catalyst. In some embodiments, the second catalyst is selected from the group consisting of $Pd(PPh_3)_4$, $Pd(OAc)_2$/SPhos, Pd(dppf)$Cl_2$, Pd(dppf)$Cl_2$·DCM, XPhos Pd G2, and $Pd_2(dba)_3$. In some embodiments, the second catalyst is $Pd(PPh_3)_4$.

In some embodiments, provided herein is a compound of Formula (II), or a pharmaceutically acceptable salt, hydrate, enantiomer, stereoisomer, or tautomer thereof, prepared by a process described herein.

In some embodiments, the compound of Formula (II) is present in the pharmaceutically acceptable formulation as a hydrate form (the compound of Formula (II)·$nH_2O$). For example, the hydrate form is a hemihydrate form, a monohydrate form, a sesquihydrate form, a dihydrate form, a trihydrate form, a tetrahydrate form, a pentahydrate form, a hexahydrate form, a heptahydrate form, an octahydrate form, a nonahydrate form, or a decahydrate form. In some embodiments, the hydrate form is a hemihydrate form, a monohydrate form, a sesquihydrate form, a dihydrate form, a trihydrate form, or a tetrahydrate form. In some embodiments, the hydrate form is a hemihydrate form. In some embodiments, the hydrate form is a monohydrate form. In some embodiments, the hydrate form is a dihydrate form. In some embodiments, the compound of Formula (II) is present in a composition or a pharmaceutically acceptable composition as a dihydrate form.

In some embodiments, the compound of Formula (II), when prepared by a process described herein, is obtained in a composition comprising the compound of Formula (II) and a compound of Formula (XIV):

(XIV)

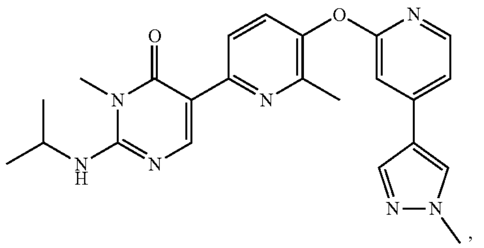

wherein the amount of the compound of Formula (XIV) present in the composition is undetectable or is no more than about 5% weight/weight of the composition.

In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 4.5% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 4% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 3.5% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 3% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 2.5% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 2% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 1.5% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 1% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.9% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.8% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.7% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.6% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.5% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.4% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.3% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.2% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.15% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.1% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.09% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.08% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.07% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.06% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.05% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.04% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.03% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.02% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.015% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable or is no more than about 0.01% weight/weight of the composition. In some embodiments, the compound of Formula (II), when prepared by a process described herein, is obtained in a composition comprising the compound of Formula (II) and a compound of Formula (XIV) wherein the amount of the compound of Formula (XIV) present in the composition is undetectable.

In some embodiments, provided herein is a compound of Formula (II):

(II)

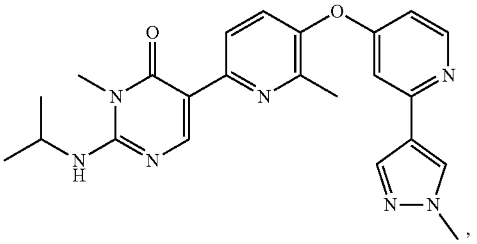

or a pharmaceutically acceptable salt, hydrate, enantiomer, stereoisomer, or tautomer thereof, having an undetectable amount to no more than about 5% area under the curve when measured by HPLC of a compound of Formula (XIV):

(XIV)

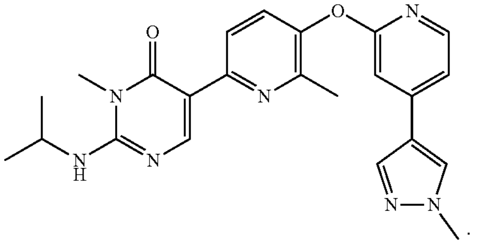

In some embodiments, the compound of Formula (II), or a pharmaceutically acceptable salt, hydrate, enantiomer, stereoisomer, or tautomer thereof, is characterized as having an undetectable amount to no more than about 4.5% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 4% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 3.5% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 3% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 2.5% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 2% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 1.5% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 1% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.5% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.4% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.3% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.2% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.15% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.1% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.09% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.08% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.07% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.06% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.05% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.04% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.03% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.02% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.015% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount to no more than about 0.01% area under the curve when measured by HPLC of a compound of Formula (XIV). In some embodiments, the compound of Formula (II), or a pharmaceutically acceptable salt, hydrate, enantiomer, stereoisomer, or tautomer thereof, is characterized as having an undetectable amount a compound of Formula (XIV).

In some embodiments, provided herein are compositions, comprising a compound of Formula (II):

(II)

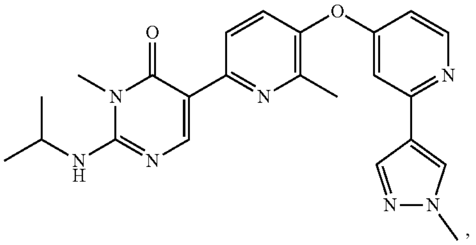

having a purity of greater than or equal to about 99.8% area under the curve when measured by HPLC, and a compound of Formula (XIV):

(XIV)

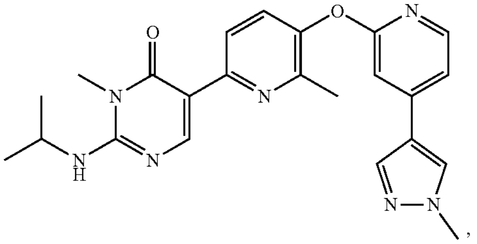

wherein the compound of Formula (XIV) is present in the composition at no more than about 0.2% area under the curve when measured by HPLC.

In some embodiments, the compound of Formula (XIV) is present in the composition at no more than about 0.15% area under the curve when measured by HPLC. In some embodiments, the compound of Formula (XIV) is present in the composition at no more than about 0.1% area under the curve when measured by HPLC. In some embodiments, the compound of Formula (XIV) is present in the composition at no more than about 0.05% area under the curve when measured by HPLC. In some embodiments, the compound of Formula (XIV) is present in the composition at no more than about 0.04% area under the curve when measured by HPLC. In some embodiments, the compound of Formula (XIV) is present in the composition at no more than about 0.03% area under the curve when measured by HPLC. In some embodiments, the compound of Formula (XIV) is present in the composition at no more than about 0.02% area under the curve when measured by HPLC. In some embodiments, the compound of Formula (XIV) is present in the composition at no more than about 0.015% area under the curve when measured by HPLC. In some embodiments, the compound of Formula (XIV) is present in the composition at no more than about 0.01% area under the curve when measured by HPLC.

Formula (III)

In some embodiments, provided herein are processes of preparing a compound of Formula (III):

(III)

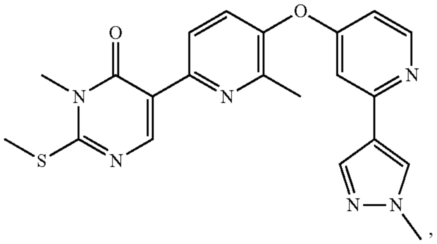

the process comprising:

reacting a compound of Formula (IX):

(IX)

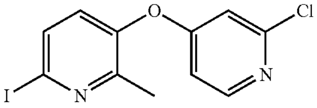

wherein the compound of Formula (IX) is optionally prepared by a process described herein, with a compound of Formula (XII):

(XII)

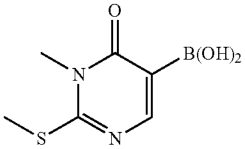

in the presence of a first catalyst to produce a compound of Formula (IV):

(IV)

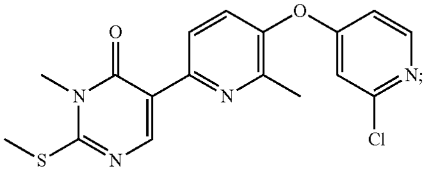

reacting the compound of Formula (IV) with a compound represented by:

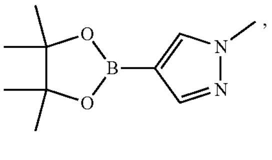

in the presence of a second catalyst, thereby preparing the compound of Formula (III).

In some embodiments, the first catalyst is a palladium catalyst. In some embodiments, the first catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$. In some embodiments, the first catalyst is $Pd(PPh_3)_4$.

In some embodiments, the second catalyst is a palladium catalyst. In some embodiments, the second catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$. In some embodiments, the second catalyst is $Pd(PPh_3)_4$.

In some embodiments, provided herein is a compound of Formula (III) prepared by a process described herein.

In some embodiments, the compound of Formula (III) is obtained in a composition comprising the compound of Formula (III) and a compound of Formula (XV):

(XV)

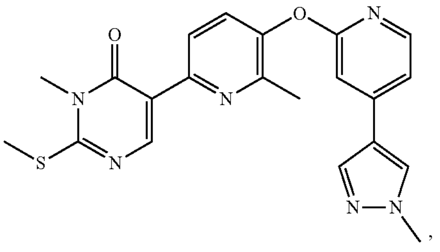

wherein the amount of the compound of Formula (XV) present in the composition is undetectable or is no more than about 10% weight/weight of the composition.

In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 9.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 9% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 8.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 8% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 7.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 7% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 6.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 6% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 5.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 4.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 4% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 3.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 3% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 2.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 2% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 1.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 1% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.9% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.8% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.7% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.6% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.5% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.4% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.3% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.2% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.15% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.1% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.09% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.08% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.07% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.06% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.05% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.04% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.03% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.02% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.015% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable or is no more than about 0.01% weight/weight of the composition. In some embodiments, the compound of Formula (III), when prepared by a process described herein, is obtained in a composition comprising the compound of Formula (III) and a compound of Formula (XV) wherein the amount of the compound of Formula (XV) present in the composition is undetectable.

In some embodiments, provided herein is a compound of Formula (III):

(III)

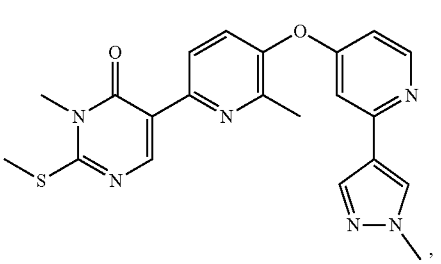, having an undetectable amount to no more than about 5% area under the curve when measured by HPLC of a compound of Formula (XV):

(XV)

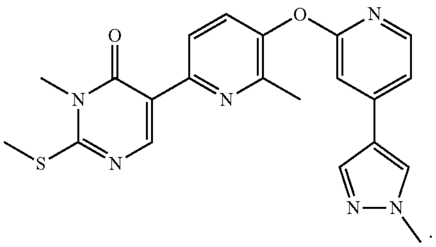.

In some embodiments, the compound of Formula (III), or a pharmaceutically acceptable salt, enantiomer, stereoisomer, or tautomer thereof, is characterized as having an undetectable amount to no more than about 4.5% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 4% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 3.5% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 3% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 2.5% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 2% area under the curve when measured by HPLC of a compound of Formula (XV).

In some embodiments, the compound of Formula (III), or a pharmaceutically acceptable salt, enantiomer, stereoisomer, or tautomer thereof, is characterized as having an undetectable amount to no more than about 1.5% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 1% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.5% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.4% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.3% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.2% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.15% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.1% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.09% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.08% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.07% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.06% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.05% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.04% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.03% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.02% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.015% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount to no more than about 0.01% area under the curve when measured by HPLC of a compound of Formula (XV). In some embodiments, the compound of Formula (III), or a pharmaceutically acceptable salt, enantiomer, stereoisomer, or tautomer thereof, is characterized as having an undetectable amount a compound of Formula (XV).

Also provided herein, in some embodiments, are compositions, comprising a compound of Formula (III):

(III)

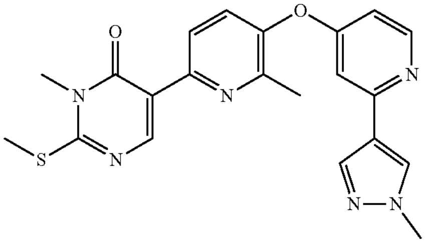

, having a purity of greater than or equal to about 99.8% area under the curve when measured by HPLC, and a compound of Formula (XV), wherein the compound of Formula (XV) is present in the composition at no more than about 0.2% area under the curve when measured by HPLC.

In some embodiments, the compound of Formula (XV) is present in the composition at no more than about 0.15% area under the curve when measured by HPLC. In some embodiments, the compound of Formula (XV) is present in the composition at no more than about 0.1% area under the curve when measured by HPLC. In some embodiments, the compound of Formula (XV) is present in the composition at no more than about 0.05% area under the curve when measured by HPLC. In some embodiments, the compound of Formula (XV) is present in the composition at no more than about 0.04% area under the curve when measured by HPLC. In some embodiments, the compound of Formula (XV) is present in the composition at no more than about 0.03% area under the curve when measured by HPLC. In some embodiments, the compound of Formula (XV) is present in the composition at no more than about 0.02% area under the curve when measured by HPLC. In some embodiments, the compound of Formula (XV) is present in the composition at no more than about 0.015% area under the curve when measured by HPLC. In some embodiments, the compound of Formula (XV) is present in the composition at no more than about 0.01% area under the curve when measured by HPLC.

Formula (IV)

In some embodiments, provided herein are processes of preparing a compound of Formula (IV):

(IV)

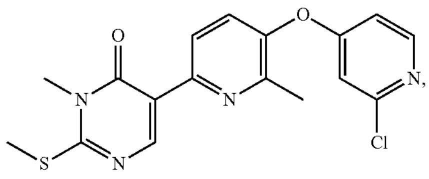

, the process comprising:

reacting a compound of Formula (IX):

(IX)

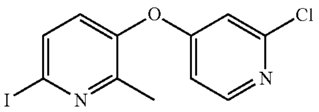

wherein the compound of Formula (IX) is optionally prepared by a process described herein, with a compound of Formula (XII):

(XII)

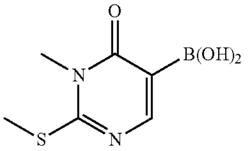

in the presence of a catalyst, thereby preparing the compound of Formula (IV).

In some embodiments, the catalyst is a palladium catalyst. In some embodiments, the catalyst is selected from the group consisting of $Pd(PPh_3)_4$, $Pd(OAc)_2$/SPhos, Pd(dppf)$Cl_2$, Pd(dppf)$Cl_2$·DCM, XPhos Pd G2, and $Pd_2(dba)_3$. In some embodiments, the catalyst is $Pd(PPh_3)_4$.

In some embodiments, provided herein is a compound of Formula (IV) prepared by a process described herein.

In some embodiments, the compound of Formula (IV), when prepared by a process described herein, is obtained in a composition comprising the compound of Formula (IV) and a compound of Formula (XVI):

(XVI)

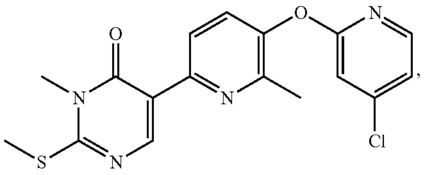

wherein the amount of the compound of Formula (XVI) present in the composition is undetectable or is no more than about 20% weight/weight of the composition.

In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 19% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 18% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 17% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 16% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 15% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 14% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 13% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 12% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 11% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 10% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 9% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 8% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 7% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 6% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 4.5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 4% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 3.5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 3% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 2.5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 2% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 1.5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 1% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.9% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.8% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.7% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.6% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.5% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.4% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.3% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.2% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.15% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.1% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.09% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.08% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.07% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.06% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.05% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.04% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.03% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.02% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.015% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable or is no more than about 0.01% weight/weight of the composition. In some embodiments, the compound of Formula (IV), when prepared by a process described herein, is obtained in a composition comprising the compound of Formula (IV) and a compound of Formula (XVI) wherein the amount of the compound of Formula (XVI) present in the composition is undetectable.

In some embodiments, provided herein is a compound of Formula (IV):

(IV)

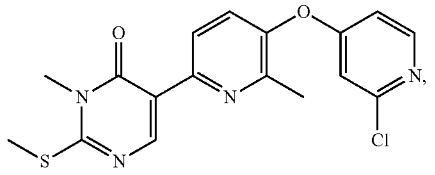

having an undetectable amount to no more than about 5% area under the curve when measured by HPLC of a compound of Formula (XVI):

(XVI)

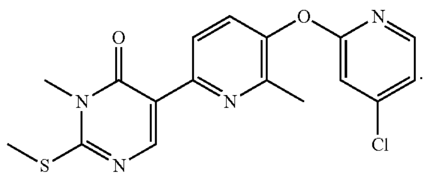

In some embodiments, the compound of Formula (IV), or a pharmaceutically acceptable salt, enantiomer, stereoisomer, or tautomer thereof, is characterized as having an undetectable amount to no more than about 4.5% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 4% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 3.5% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 3% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 2.5% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 2% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 1.5% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 1% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.5% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.4% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.3% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.2% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.15% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.1% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.09% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.08% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.07% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.06% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.05% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.04% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.03% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.02% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.015% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount to no more than about 0.01% area under the curve when measured by HPLC of a compound of Formula (XVI). In some embodiments, the compound of Formula (IV), or a pharmaceutically acceptable salt, enantiomer, stereoisomer, or tautomer thereof, is characterized as having an undetectable amount a compound of Formula (XVI).

In some embodiments, provided herein are compositions, comprising a compound of Formula (IV):

(IV)

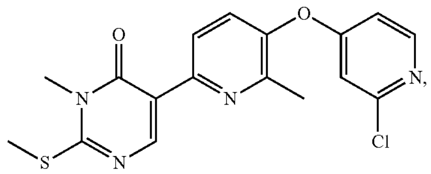

having a purity of greater than or equal to about 99.8% area under the curve when measured by HPLC, and a compound of Formula (XVI):

(XVI)

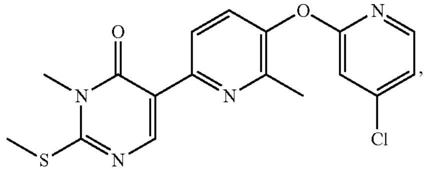

wherein the compound of Formula (XVI) is present in the composition at no more than about 0.2% area under the curve when measured by HPLC.

In some embodiments, the compound of Formula (XVI) is present in the composition at no more than about 0.15% area under the curve when measured by HPLC. In some embodiments, the compound of Formula (XVI) is present in the composition at no more than about 0.1% area under the curve when measured by HPLC. In some embodiments, the compound of Formula (XVI) is present in the composition at no more than about 0.05% area under the curve when measured by HPLC. In some embodiments, the compound of Formula (XVI) is present in the composition at no more than about 0.04% area under the curve when measured by HPLC. In some embodiments, the compound of Formula (XVI) is present in the composition at no more than about 0.03% area under the curve when measured by HPLC. In some embodiments, the compound of Formula (XVI) is present in the composition at no more than about 0.02% area under the curve when measured by HPLC. In some embodiments, the compound of Formula (XVI) is present in the composition at no more than about 0.015% area under the curve when measured by HPLC. In some embodiments, the compound of Formula (XVI) is present in the composition at no more than about 0.01% area under the curve when measured by HPLC.

Formula (V)

Provided herein, in some embodiments, are processes of making a compound of Formula (V):

(V)

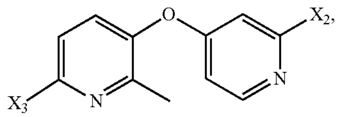

wherein $X_2$ and $X_3$ are each independently halogen, the process comprising reacting a compound of Formula (VI):

(VI)

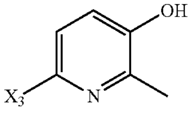

with a compound of Formula (VII):

(VII)

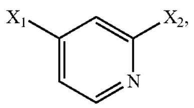

wherein $X_1$ is selected from the group consisting of F, Br, and I, in the presence of a base and a solvent, thereby preparing the compound of Formula (V).

In some embodiments, $X_1$ is F.

In some embodiments, $X_2$ is Cl.

In some embodiments, the base is selected from the group consisting of $K_2CO_3$, $Cs_2CO_3$, DBU, t-BuOK, DBN, and DIPEA.

In some embodiments, the solvent is an N,N-disubstituted amide.

In some embodiments, the solvent is selected from the group consisting of DMSO, DMAc, DMF, NMP, sulfolane, MIBK, acetonitrile, and toluene.

In some embodiments, the solvent is selected from the group consisting of DMSO, DMAc, NMP, and sulfolane.

In some embodiments, the process occurs at a temperature of about 80° C. to about 120° C. In some embodiments, the process occurs at a temperature of about 90° C. to about 120° C. In some embodiments, the process occurs at a temperature of about 100° C. to about 120° C. In some embodiments, the process occurs at a temperature of about 80° C. to about 110° C. In some embodiments, the process occurs at a temperature of about 90° C. to about 110° C. In some embodiments, the process occurs at a temperature of about 100° C. to about 110° C.

In some embodiments, the process occurs at a temperature of about 80° C., 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., 100° C., 101° C., 102° C., 103° C., 104° C., 105° C., 106° C., 107° C., 109° C., 110° C., 111° C., 112° C., 113° C., 114° C., 115° C., 116° C., 117° C., 118° C., 119° C., or 120° C.

In some embodiments, the process occurs at a temperature of about 80° C. In some embodiments, the process occurs at a temperature of about 85° C. In some embodiments, the process occurs at a temperature of about 90° C. In some embodiments, the process occurs at a temperature of about 95° C. In some embodiments, the process occurs at a temperature of about 100° C. In some embodiments, the process occurs at a temperature of about 105° C. In some embodiments, the process occurs at a temperature of about 110° C. In some embodiments, the process occurs at a temperature of about 115° C. In some embodiments, the process occurs at a temperature of about 120° C.

In some embodiments, provided herein is a compound of Formula (V) prepared by a process described herein.

Formula (IX)

In some embodiments, provided herein is a process of preparing a compound of Formula (IX):

(IX)

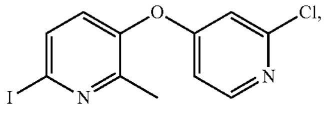

the process comprising reacting a compound of Formula (X):

(X)

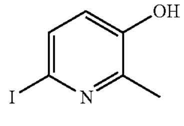

with a compound of Formula (XI):

(XI)

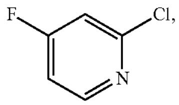

and a means for heating the reaction mixture at an elevated temperature to perform the reaction.

In some embodiments, provided herein is a process of preparing a compound of Formula (IX):

(IX)

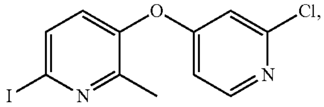

the process comprising reacting a compound of Formula (X):

(X)

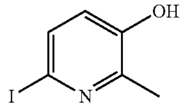

with a compound of Formula (XI):

(XI)

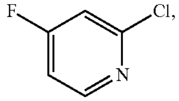

and a means for combining the mixture of the compound of Formula (X) and the compound of Formula (XI) to perform the reaction.

In some embodiments, provided herein is a process of preparing a compound of Formula (IX):

(IX)

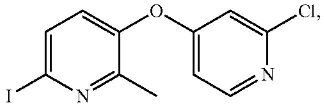

the process comprising reacting a compound of Formula (X):

(X)

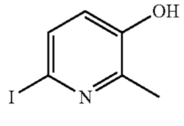

with a compound of Formula (XI):

(XI)

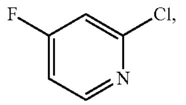

and a means for acting as a base to perform the reaction.

In some embodiments, provided herein is a process of preparing a compound of Formula (IX'):

(IX')

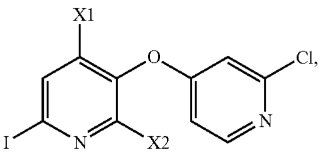

wherein X1 and X2 are each independently selected from the group consisting of H and alkyl, the process comprising reacting a compound of Formula (X'):

(X')

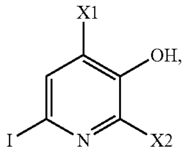

wherein X1 and X2 are as defined above for the compound of Formula (IX'), with a compound of Formula (XI):

(XI)

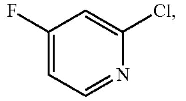

and a means for performing the reaction.

In some embodiments, provided herein is a composition, comprising a compound of Formula (IX):

(IX)

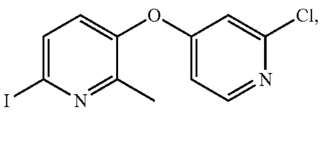

having a purity of greater than or equal to about 99.8% area under the curve when measured by HPLC, and a compound of Formula (XIII):

(XIII)

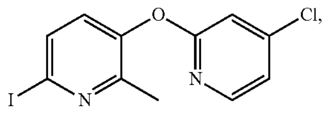

wherein the compound of Formula (XIII) is present in the composition at no more than about 0.2% area under the curve when measured by HPLC, and a means for preparing the compound of Formula (IX).

In some embodiments, provided herein is a process of preparing a compound of Formula (IX):

(IX)

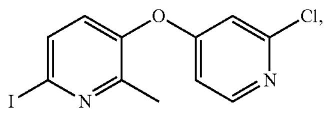

the process comprising reacting a compound of Formula (X):

(X)

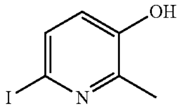

with a compound of Formula (XI):

(XI)

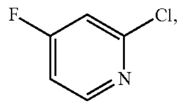

and a means for controlling the amount of the compound of Formula (XIII):

(XIII)

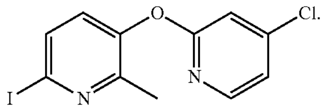

Pharmaceutical Compositions

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier.

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier.

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 2 mg of the compound of Formula (I) or (II).

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 2 mg of the compound of Formula (I) or (II).

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 10 mg of the compound of Formula (I) or (II).

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 10 mg of the compound of Formula (I) or (II).

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 14 mg of the compound of Formula (I) or (II).

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 14 mg of the compound of Formula (I) or (II).

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 20 mg of the compound of Formula (I) or (II).

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 20 mg of the compound of Formula (I) or (II).

In some embodiments, provided herein are pharmaceutical compositions comprising a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 30 mg of the compound of Formula (I) or (II).

In some embodiments, provided herein are pharmaceutical compositions consisting essentially of a compound of Formula (I) or (II), or a pharmaceutically acceptable salt, enantiomer, stereoisomer, tautomer, or hydrate thereof, and a pharmaceutically acceptable carrier, wherein the compound of Formula (I) or (II), or a pharmaceutically acceptable salt, enantiomer, stereoisomer, tautomer, or hydrate thereof, is present in the pharmaceutical composition in an amount to provide about 30 mg of the compound of Formula (I) or (II).

In some embodiments, provided herein are oral dosage forms comprising a compound of Formula (I) or (II), or a pharmaceutically acceptable salt, enantiomer, stereoisomer, tautomer, or hydrate thereof, and a pharmaceutically acceptable carrier.

In some embodiments, provided herein are oral dosage forms consisting essentially of a compound of Formula (I) or (II), or a pharmaceutically acceptable salt, enantiomer, stereoisomer, tautomer, or hydrate thereof, and a pharmaceutically acceptable carrier.

In some embodiments, the oral dosage form is a tablet or a capsule. In some embodiments, the oral dosage form is a capsule. In some embodiments, the oral dosage form is a tablet.

The pharmaceutical compositions provided herein can contain one or more fillers, which are added, for example, to increase the bulk weight of the blend resulting in a practical size for encapsulation or compression. Fillers that may be used include, but are not limited to, calcium phosphate, dicalcium phosphate, dicalcium phosphate dihydrate, calcium sulfate, calcium sulfate dihydrate, starch, calcium carbonate, magnesium carbonate, magnesium oxide, kaolin (natural hydrated aluminum silicate), sodium chloride, partially gelatinized starch, anhydrous lactose, lactose monohydrate, lactose dihydrate, trehalose dihydrate, spray dried lactose, sucrose, dextrose, dextrates, dextrin, cellulose, microcrystalline cellulose, silicified microcrystalline cellulose, powdered cellulose, partially depolymerized cellulose, mannitol, granulated mannitol, spray dried mannitol, maltodextrin, maltitol, confectioner's sugar, compressible sugar, sorbitol, starch and talc.

A disintegrant may be present in an amount necessary to expedite dissolution (e.g., increase the rate of tablet or capsule disintegration). The term "disintegrant" as used herein refers to an excipient which can oppose the physical forces of particle bonding in a tablet or capsule when the oral formulation is placed in an aqueous environment. Disintegrants include, but are not limited to, sodium starch glycolate, pregelatinized starch, clay, cellulose, alginic acid, alginate gum, polyvinylpyrrolidone, cross-linked polyvinylpyrrolidone, cross-linked calcium carboxymethylcellulose, cross-linked sodium carboxymethylcellulose, sodium croscarmellose, sodium carmellose, low substituted hydroxypropyl cellulose, low substituted hydroxypropyl cellulose sodium, guar gum, magnesium aluminum silicate, polacrilin potassium, powdered cellulose, sodium alginate and soy polysaccharide.

The pharmaceutical compositions can also include a lubricant. The term "lubricant" as used herein is typically added to prevent the tablet or capsule materials from sticking to punches or pins, minimize friction during tablet compression or encapsulation, and to allow for removal of the compressed tablet from the die or improve flowability of blends in capsules for improved processing properties. Examples of lubricants include, but are not limited to, colloidal silica, magnesium trisilicate, talc, magnesium carbonate, magnesium oxide, glyceryl behaptate, mono, di and tri glyceryl behenate, bees wax, behenoyl polyoxyl-8 glycerides, hydrogenated vegetable oil, polyethylene glycol, ethylene oxide polymer, copolymer comprising poly(ethylene oxide) and poly(propylene oxide) (such as poloxomer 188), copolymer comprising polypropylene glycol and polyethylene glycol (such as poloxomer 407), sodium lauryl sulfate, magnesium stearate, aluminum stearate, calcium stearate, sodium stearyl fumarate, stearic acid, magnesium lauryl stearate, mixtures of magnesium stearate with sodium lauryl sulfate.

Flavoring agents and flavor enhancers may also be added for the dosage form to be more palatable to the patient. Common flavoring agents and flavor enhancers for pharmaceutical products that can be included in the formulation of the present disclosure include maltol, vanillin, ethyl vanillin, menthol, citric acid, fumaric acid, ethyl maltol, and tartaric acid.

Solid and liquid formulations can also be dyed using any pharmaceutically acceptable colorant to improve their appearance and/or facilitate patient identification of the product and unit dosage level.

In liquid formulations of the present disclosure, the active ingredient and any other solid excipients may be dissolved or suspended in a liquid carrier such as water, vegetable oil, alcohol, polyethylene glycol, propylene glycol, or glycerin.

Liquid formulations can contain emulsifying agents to disperse uniformly throughout the formulation an active ingredient or other excipient that is not soluble in the liquid carrier. Emulsifying agents that can be useful in liquid formulations of the present disclosure include, for example, gelatin, egg yolk, casein, cholesterol, acacia, tragacanth, chondrus, pectin, methyl cellulose, carbomer, cetostearyl alcohol, and cetyl alcohol.

Liquid formulations of the present disclosure can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid formulation can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid formulations of the present disclosure include powders, granulates, aggregates, and compacted formulations. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present disclosure is oral.

Diluents increase the bulk of a solid formulation and can make a pharmaceutical dosage form containing the formulation easier for the patient and caregiver to handle. Diluents for solid formulations include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol, and talc.

Solid formulations that are compacted into a dosage form, such as a tablet, can include excipients whose functions include helping to bind the active ingredient and other excipients together after compression. Binders for solid formulations include acacia, alginic acid, carbomer (e.g., Carbopol), carboxymethylcellulose sodium, dextrin, ethyl cellulose, gelatin, guar gum, hydrogenated vegetable oil, hydroxyethyl cellulose, hydroxypropyl cellulose (e.g., Klucel®), hydroxypropyl methyl cellulose (e.g., Methocel®), liquid glucose, magnesium aluminum silicate, maltodextrin, methylcellulose, polymethacrylates, povidone (e.g., Kollidon®, Plasdone®), pregelatinized starch, sodium alginate, and starch.

The dissolution rate of a compacted solid formulation in the patient's stomach can be increased by the addition of a disintegrant to the formulation. Disintegrants include alginic acid, carboxymethylcellulose calcium, carboxymethylcellulose sodium (e.g., Ac-Di-Sol®, Primellose®), colloidal silicon dioxide, croscarmellose sodium, Crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®), and starch.

Glidants can be added to improve the flowability of a non-compacted solid formulation and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered formulation, the formulation is subjected to pressure from a punch and dye. Some excipients and active ingredients tend to adhere to the surfaces of the punch and dye, which can cause the product to have pitting and other surface irregularities. A lubricant can be added to the formulation to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

A formulation for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting formulation can be prepared conventionally by dry blending. For example, the blended formulation of the actives and excipients can be compacted into a slug or a sheet and then comminuted into compacted granules. The compacted granules can subsequently be compressed into a tablet.

As an alternative to dry granulation, a blended formulation can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

Dosage forms include solid dosage forms like tablets, powders, capsules, suppositories, sachets, troches, and lozenges, as well as liquid syrups, suspensions, and elixirs.

The dosage form of the present disclosure can be a capsule containing the formulation, such as a powdered or granulated solid formulation of the disclosure, within either a hard or soft shell. The shell can be made from gelatin and optionally contain a plasticizer such as glycerin and sorbitol, and an opacifying agent or colorant.

In further embodiments, a pharmaceutical formulation of the compound represented by Formula (I) is formulated for administration to a mammal, such as a human. The compound represented by Formula (I) can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringe ability), fluidity, boiling point, miscibility, and purity. Suitable solvents include alcohol USP (United States Pharmacopeia), benzyl alcohol NF, benzyl benzoate USP, and Castor oil USP. Additional substances can be added to the formulation such as buffers, solubilizers, and antioxidants, among others. Ansel et al, Pharmaceutical Dosage Forms and Drug Delivery Systems, $7^{th}$ ed.

Methods of Use

Provided herein, in part, are methods for the treatment or prevention of a variety of diseases and disorders, which comprise administering to a patient in need of such treatment or prevention a therapeutically effective amount of a compound represented by Formula (I) or (II), or a pharmaceutically acceptable salt, hydrate, enantiomer, stereoisomer, or tautomer thereof, a composition comprising a compound represented by Formula (I) or (II), or a pharmaceutically acceptable salt, hydrate, enantiomer, stereoisomer, or tautomer thereof, or an oral dosage form comprising a compound represented by Formula (I) or (II), or a pharmaceutically acceptable salt, hydrate, enantiomer, stereoisomer, or tautomer thereof.

In some embodiments, provided herein is a method of treating a tenosynovial giant cell tumor in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, the tenosynovial giant cell tumor is a diffuse-type tenosynovial giant cell tumor.

In some embodiments, the tenosynovial giant cell tumor is a localized tenosynovial giant cell tumor.

In some embodiments, provided herein is a method of treating graft versus host disease (GVHD) in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, the graft versus host disease is chronic graft versus host disease (cGVHD).

In some embodiments, the graft versus host disease is acute graft versus host disease (aGVHD).

In some embodiments, provided herein is a method of treating a neurodegenerative disease or condition in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a method of treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, the solid tumor has progressed after prior administration of another cancer therapy.

Also provided herein, in some embodiments, is a method of treating tumors known to have expression of colony-stimulating factor 1 receptor (CSF-1R) or its ligands, colony stimulating factor-1 (CSF-1), or interleukin (IL)-34 (IL-34), in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, provided herein is a method of treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof, comprising administering to the patient a therapeutically effective amount of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein.

In some embodiments, the methods described herein further comprise administering to the patient a therapeutically effective amount of one or more additional therapeutic agents.

In some embodiments, the methods described herein further comprise administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine.

In some embodiments, the one or more additional therapeutic agents is belumosudil.

In some embodiments, the methods described herein further comprise administering an immunomodulatory therapeutic.

In some embodiments, the methods described herein further comprise administering a chemotherapeutic agent.

In some embodiments, the methods described herein further comprise administering an immunomodulatory therapeutic and a chemotherapeutic agent.

In some embodiments, the compound of Formula (I) or (II), or a pharmaceutically acceptable salt, hydrate, enantiomer, stereoisomer, or tautomer thereof, the composition described herein, or the pharmaceutical composition described herein, is administered orally.

In some embodiments, provided herein is a compound of Formula (I) or (II), or a pharmaceutically acceptable salt, hydrate, enantiomer, stereoisomer, or tautomer thereof, the composition described herein, the pharmaceutical composition described herein, or the oral dosage form described herein for use in treating a tenosynovial giant cell tumor in a patient in need thereof.

In some embodiments, provided herein is a compound of Formula (I) or (II), or pharmaceutically acceptable salt, hydrate, enantiomer, stereoisomer, or tautomer thereof, composition, pharmaceutical composition, or oral dosage form for use in treating a tenosynovial giant cell tumor in a patient in need thereof, wherein the tenosynovial giant cell tumor is a diffuse-type tenosynovial giant cell tumor.

In some embodiments, provided herein is a compound of Formula (I) or (II) or pharmaceutically acceptable salt, hydrate, enantiomer, stereoisomer, or tautomer thereof, composition, pharmaceutical composition, or oral dosage form for use in treating a tenosynovial giant cell tumor in a patient in need thereof, wherein the tenosynovial giant cell tumor is a localized tenosynovial giant cell tumor.

In some embodiments, provided herein is a compound of Formula (I) or (II), or a pharmaceutically acceptable salt, hydrate, enantiomer, stereoisomer, or tautomer thereof, the composition described herein, the pharmaceutical composition described herein, or an oral dosage form described herein, for use in treating graft versus host disease (GVHD) in a patient in need thereof.

In some embodiments, provided herein is a compound of Formula (I) or (II), or pharmaceutically acceptable salt, hydrate, enantiomer, stereoisomer, or tautomer thereof, composition, pharmaceutical composition, or oral dosage form for use in treating graft versus host disease (GVHD) in a patient in need thereof, wherein the graft versus host disease is chronic graft versus host disease (cGVHD).

In some embodiments, provided herein is a compound of Formula (I) or (II), or pharmaceutically acceptable salt, hydrate, enantiomer, stereoisomer, or tautomer thereof, composition, pharmaceutical composition, or oral dosage form for use in treating graft versus host disease (GVHD) in a patient in need thereof, wherein the graft versus host disease is acute graft versus host disease (aGVHD).

In some embodiments, provided herein is a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, for use in treating a neurodegenerative disease or condition in a patient in need thereof.

In some embodiments, provided herein is a compound or pharmaceutically acceptable salt, hydrate, enantiomer, stereoisomer, or tautomer thereof, composition, pharmaceutical composition, or oral dosage form for use in treating a neurodegenerative disease or condition in a patient in need thereof, wherein the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein, for use in treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof.

In some embodiments, provided herein is a compound or pharmaceutically acceptable salt, hydrate, enantiomer, stereoisomer, or tautomer thereof, composition, pharmaceutical composition, or oral dosage form for use in treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof, wherein the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is a compound or pharmaceutically acceptable salt, hydrate, enantiomer, stereoisomer, or tautomer thereof, composition, pharmaceutical composition, or oral dosage form for use in a treatment described herein, wherein the solid tumor has progressed after prior administration of another cancer therapy.

In some embodiments, provided herein is a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, for use in treating tumors known to have expression of colony-stimulating factor 1 receptor (CSF-1R) or its ligands, colony stimulating factor-1 (CSF-1), or interleukin (IL)-34 (IL-34), in a patient in need thereof.

In some embodiments, provided herein is a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, for use in treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof.

In some embodiments, provided herein is a compound or pharmaceutically acceptable salt, hydrate, enantiomer, stereoisomer, or tautomer thereof, composition, pharmaceutical composition, or oral dosage form for use described herein, further comprising administering to the patient a therapeutically effective amount of one or more additional therapeutic agents.

In some embodiments, provided herein is a compound or pharmaceutically acceptable salt, hydrate, enantiomer, stereoisomer, or tautomer thereof, composition, pharmaceutical composition, or oral dosage form for use described herein, further comprising administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine.

In some embodiments, provided herein is a compound or pharmaceutically acceptable salt, hydrate, enantiomer, stereoisomer, or tautomer thereof, composition, pharmaceutical composition, or oral dosage form for use described herein, wherein the one or more additional therapeutic agents is belumosudil.

In some embodiments, provided herein is a compound for use or pharmaceutical composition for use described herein, further comprising administering an immunomodulatory therapeutic.

In some embodiments, provided herein is a compound or pharmaceutically acceptable salt, hydrate, enantiomer, stereoisomer, or tautomer thereof, composition, pharmaceutical composition, or oral dosage form for use described herein, further comprising administering a chemotherapeutic agent.

In some embodiments, provided herein is a compound for use or pharmaceutical composition for use described herein, further comprising administering an immunomodulatory therapeutic and a chemotherapeutic agent.

In some embodiments, provided herein is a compound or pharmaceutically acceptable salt, hydrate, enantiomer, stereoisomer, or tautomer thereof, composition, pharmaceutical composition, or oral dosage form for use described herein, wherein the compound of Formula (I) and (II), or a pharmaceutically acceptable salt, hydrate, enantiomer, stereoisomer, or tautomer thereof, the composition described herein, or the pharmaceutical composition described herein, is administered orally.

In some embodiments, provided herein is the use of a compound of Formula (I) or (II), or a pharmaceutically acceptable salt, hydrate, enantiomer, stereoisomer, or tautomer thereof, the composition described herein, the pharmaceutical composition described herein, or the oral dosage form described herein in the manufacture of a medicament for treating a tenosynovial giant cell tumor in a patient in need thereof.

In some embodiments, provided herein is the use of a compound of Formula (I) or (II), or pharmaceutically acceptable salt, hydrate, enantiomer, stereoisomer, or tautomer thereof, composition, pharmaceutical composition, or oral dosage form in the manufacture of a medicament for treating a tenosynovial giant cell tumor in a patient in need thereof, wherein the tenosynovial giant cell tumor is a diffuse-type tenosynovial giant cell tumor.

In some embodiments, provided herein is the use of a compound of Formula (I) or (II) or pharmaceutically acceptable salt, hydrate, enantiomer, stereoisomer, or tautomer thereof, composition, pharmaceutical composition, or oral dosage form in the manufacture of a medicament for treating a tenosynovial giant cell tumor in a patient in need thereof, wherein the tenosynovial giant cell tumor is a localized tenosynovial giant cell tumor.

In some embodiments, provided herein is the use of a compound of Formula (I) or (II), or a pharmaceutically acceptable salt, hydrate, enantiomer, stereoisomer, or tautomer thereof, the composition described herein, the pharmaceutical composition described herein, or an oral dosage form described herein, in the manufacture of a medicament for treating graft versus host disease (GVHD) in a patient in need thereof.

In some embodiments, provided herein is the use of a compound of Formula (I) or (II), or pharmaceutically acceptable salt, hydrate, enantiomer, stereoisomer, or tautomer thereof, composition, pharmaceutical composition, or oral dosage form in the manufacture of a medicament for treating graft versus host disease (GVHD) in a patient in need thereof, wherein the graft versus host disease is chronic graft versus host disease (cGVHD).

In some embodiments, provided herein is the use of a compound of Formula (I) or (II), or pharmaceutically acceptable salt, hydrate, enantiomer, stereoisomer, or tautomer thereof, composition, pharmaceutical composition, or oral dosage form in the manufacture of a medicament for treating graft versus host disease (GVHD) in a patient in need thereof, wherein the graft versus host disease is acute graft versus host disease (aGVHID).

In some embodiments, provided herein is the use of a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, in the manufacture of a medicament for treating a neurodegenerative disease or condition in a patient in need thereof.

In some embodiments, provided herein is the use of a compound or pharmaceutically acceptable salt, hydrate, enantiomer, stereoisomer, or tautomer thereof, composition, pharmaceutical composition, or oral dosage form, in the manufacture of a medicament for treating a neurodegenerative disease or condition in a patient in need thereof, wherein the neurodegenerative disease condition is selected from the group consisting of Parkinson's disease (PD), Alzheimer's Disease (AD), frontotemporal dementia (FTD), amyotrophic lateral sclerosis (ALS), mild cognitive impairment, and Huntington's Disease (HD).

In some embodiments, provided herein is the use of a compound of Formula (I) or (II), or a pharmaceutically acceptable salt, hydrate, enantiomer, stereoisomer, or tautomer thereof, a therapeutically effective amount of a composition described herein, a therapeutically effective amount of a pharmaceutical composition described herein, or a therapeutically effective amount of an oral dosage form described herein, in the manufacture of a medicament for treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof.

In some embodiments, provided herein is the use of a compound or pharmaceutically acceptable salt, hydrate, enantiomer, stereoisomer, or tautomer thereof, composition, pharmaceutical composition, or oral dosage form, in the manufacture of a medicament for treating a cancer selected from the group consisting of solid tumors, acute myeloid leukemia (AML), relapsed/refractory acute myeloid leukemia (AML), relapsed acute myeloid leukemia (AML), refractory acute myeloid leukemia (AML), myelodysplastic syndrome, acute lymphocytic leukemia (ALL), chronic lymphocytic leukemia (CLL), pancreatic ductal adenocarcinoma (PDAC), ovarian cancer, non-small cell lung cancer (NSCLC), prostate cancer, osteosarcoma, breast cancer, colon cancer, and glioblastoma, in a patient in need thereof, wherein the solid tumor is selected from the group consisting of ovarian cancer, pancreatic cancer, prostate cancer, lung cancer, breast cancer, kidney cancer, liver cancer, cervical cancer, bone metastatic cancer, papillary thyroid cancer, non-small cell lung cancer, colon cancer, and gastrointestinal stromal tumor.

In some embodiments, provided herein is the use of a compound or pharmaceutically acceptable salt, hydrate, enantiomer, stereoisomer, or tautomer thereof, composition, pharmaceutical composition, or oral dosage form described herein, in the manufacture of a medicament for treating solid tumors, wherein the solid tumor has progressed after prior administration of another cancer therapy.

In some embodiments, provided herein is the use of a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, in the manufacture of a medicament for treating tumors known to have expression of colony-stimulating factor 1 receptor (CSF-1R) or its ligands, colony stimulating factor-1 (CSF-1), or interleukin (IL)-34 (IL-34), in a patient in need thereof.

In some embodiments, provided herein is the use of a compound of Formula (I) or (II), or a pharmaceutically acceptable salt, hydrate, enantiomer, stereoisomer, or tautomer thereof, a composition described herein, a pharmaceutical composition described herein, or an oral dosage form described herein, in the manufacture of a medicament for treating a disease or condition selected from the group consisting of metabolic diseases, rheumatoid arthritis, osteoarthritis, multiple sclerosis, autoimmune nephritis, lupus, Crohn's disease, asthma, chronic obstructive pulmonary diseases, osteoporosis, hypereosinophilic syndromes, mastocytosis, and histiocytosis, in a patient in need thereof.

In some embodiments, provided herein is the use of a compound or pharmaceutically acceptable salt, hydrate, enantiomer, stereoisomer, or tautomer thereof, composition, pharmaceutical composition, or oral dosage form described herein, further comprising administering to the patient a therapeutically effective amount of one or more additional therapeutic agents.

In some embodiments, provided herein is the use of a compound or pharmaceutically acceptable salt, hydrate, enantiomer, stereoisomer, or tautomer thereof, composition, pharmaceutical composition, or oral dosage form, in the manufacture of a medicament for treatment described herein, further comprising administering to the patient a therapeutically effective amount of one or more additional therapeutic agents wherein the one or more additional therapeutic agents is selected from the group consisting of methoxsalen, abatacept, everolimus, alemtuzumab, antithymocyte globulin, autologous serum eye drops, azathioprine, belumosudil, bortezomib, mycophenolate mofetil, cyclophosphamide, cyclosporine, extracorporeal photopheresis, etanercept, imatinib mesylate, ibrutinib, interleukin-2, infliximab, ruxolitinib, methotrexate, muromab-CD3, pentostatin, denileukin diftitox, prednisone, prednisolone, tacrolimus, psoralen with ultraviolet A light, sirolimus, rituximab, methylprednisolone, budesonide, thalidomide, halofuginone, and hydroxychloroquine.

In some embodiments, provided herein is the use of a compound or pharmaceutically acceptable salt, hydrate, enantiomer, stereoisomer, or tautomer thereof, composition, pharmaceutical composition, or oral dosage form in the manufacture of a medicament for treatment described herein, wherein the one or more additional therapeutic agents is belumosudil.

In some embodiments, provided herein is the use of a compound or a pharmaceutical composition in the manufacture of a medicament for treatment described herein, further comprising administering an immunomodulatory therapeutic.

In some embodiments, provided herein is the use of a compound or pharmaceutically acceptable salt, hydrate, enantiomer, stereoisomer, or tautomer thereof, composition, pharmaceutical composition, or oral dosage form in the manufacture of a medicament for treatment described herein, further comprising administering a chemotherapeutic agent.

In some embodiments, provided herein is use of a compound or pharmaceutical composition, in the manufacture of a medicament for treatment described herein, further comprising administering an immunomodulatory therapeutic and a chemotherapeutic agent.

In some embodiments, provided herein is the use of a compound or pharmaceutically acceptable salt, hydrate, enantiomer, stereoisomer, or tautomer thereof, composition, pharmaceutical composition, or oral dosage form, in the manufacture of a medicament for treatment described herein, wherein the compound of Formula (I) and (II), or a pharmaceutically acceptable salt, hydrate, enantiomer, stereoisomer, or tautomer thereof, the composition described herein, or the pharmaceutical composition described herein, is administered orally.

EXAMPLES

The present disclosure is not to be limited in scope by the specific embodiments disclosed in the examples which are intended as illustrations of a few aspects of the disclosure and any embodiments that are functionally equivalent are within the scope of this disclosure. Indeed, various modifications in addition to those shown and described herein will become apparent to those skilled in the art and are intended to fall within the scope of the appended claims.

The following abbreviations are used in this disclosure and have the following definitions: "ADP" is adenosine diphosphate, "AUC" is area under the curve, "$Cs_2CO_3$" is cesium carbonate, "conc." is concentrated, "DBN" is 1,5-diazabicyclo(4.3.0)non-5-ene, "DBU" is 1,8-diazabicyclo[5.4.0]undec-7-ene, "DCM" is dichloromethane, "DIEA" is N,N-diisopropylethylamine, "DMA" or "DMAc" or "DMAC" is N,N-dimethylacetamide, "DMAP" is 4-(dimethylamino)pyridine, "DMF" is N,N-dimethylformamide, "dppf" is 1,1'-bis(diphenylphosphino)ferrocene, "DMEM" is Dulbecco's Modified Eagle Media, "DMSO" is dimethylsulfoxide, "DPPA" is diphenylphosphoryl azide, "ESI" is electrospray ionization, "$Et_2O$" is diethylether, "EtOAc" is ethyl acetate, "EtOH" is ethanol, "GST" is glutathione S-transferase, "h" is hour or hours, "Hex" is hexane, "$IC_{50}$" is half maximal inhibitory concentration, "$K_2CO_3$" is potassium carbonate, "LiMHDS" is lithium bis(trimethylsilyl) amide, "MeCN" is acetonitrile, "MeOH" is methanol, "MHz" is megahertz, "min" is minute or minutes, "MIBK" is methyl isobutyl ketone, "MS" is mass spectrometry, "MTBE" is methyl tert-butyl ether, "NADH" is nicotinamide adenine dinucleotide, "NBS" is N-bromosuccinimide, "NMP" is N-Methyl-2-pyrrolidone, "NMR" is nuclear magnetic resonance, "PBS" is phosphate buffered saline, "Pd/C" is palladium on carbon, "$Pd_2(dba)_3$" is tris(dibenzylideneacetone)dipalladium(O), "$Pd(PPh_3)_4$" is tetrakis(triphenylphosphine)palladium (0), "prep-HPLC" is preparative high performance liquid chromatography, "RT" is room temperature which is also known as "ambient temp," which will be understood to consist of a range of normal laboratory temperatures ranging from 15-25° C., "satd." is saturated, "sulfolane" is 1λ-Thiolane-1,1-dione, "t-BuOK" is potassium tert-butoxide, "TEA" is triethylamine, "TFA" is trifluoroacetic acid, "THF" is tetrahydrofuran, "Tris" is tris(hydroxymethyl)aminomethane, "SPhos" is dicyclohexyl(2',6'-dimethoxy[1,1'-biphenyl]-2-yl)phosphane, "Xantphos" is 4,5-bis(diphenylphosphino)-9,9-dimethylxanthene, and "X-Phos" is 2-dicyclohexylphosphino-2',4',6'-triisopropylbiphenyl.

Example 1. Exemplary Preparation of a Compound of Formula (II)

Example 1a. Preparation of a Compound of Formula (IX)

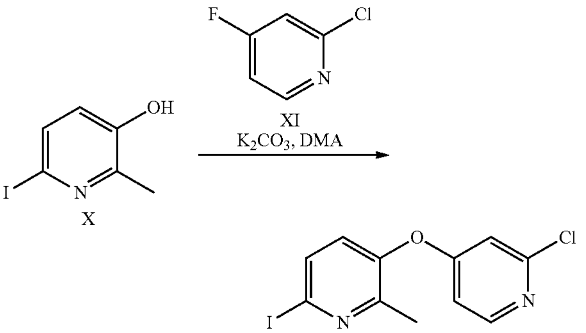

X
XI
IX 3-((2-chloropyridin-4-yl)oxy)-6-iodo-2-methylpyridine (IX): 6-iodo-2-methylpyridin-3-ol (X)(1.00 kg), 2-chloro-4-fluoropyridine (XI)(0.78 kg), dimethylacetamide (8.3 L) and potassium carbonate (0.59 kg) were charged in a reactor, and the reaction mixture was heated at about 100-105° C. for about 5 hours. The reaction mixture was then cooled to 10-20° C., quenched with deionized water, and filtered. The filter cake was washed with deionized water and dried at a temperature not more than 40° C. under vacuum. The title compound was obtained in a yield of 90% (1.3 kg). At least the temperature employed in Step 1a provides the means for heating the reaction mixture to perform the reaction. At least the solvents employed in Step 1a provide the means for combining the reaction mixture to perform the reaction. At least the base employed in Step 1a provides the means for performing the reaction. At least the temperature, solvents and base employed in Step 1a provide the means for performing the reaction. At least the temperature, solvents, and base employed in Step 1a limit the amount of the compound of Formula (XIII) isolated together with the compound of Formula (IX). At least the temperature, solvents and base employed in Step 1 provide the means for providing a composition comprising a compound of Formula (IX), wherein the compound of Formula (IX) has a purity of greater than or equal to about 99.8% area under the curve when measured by HPLC, and a compound of Formula (XIII), wherein the compound of Formula (XIII) is present in the composition at no more than about 0.2% area under the curve when measured by HPLC. At least the temperature, solvents and base employed in Step 1 provide the means for controlling the amount of the compound of Formula (XIII).

Example 1b. Preparation of a Compound of Formula (IV)

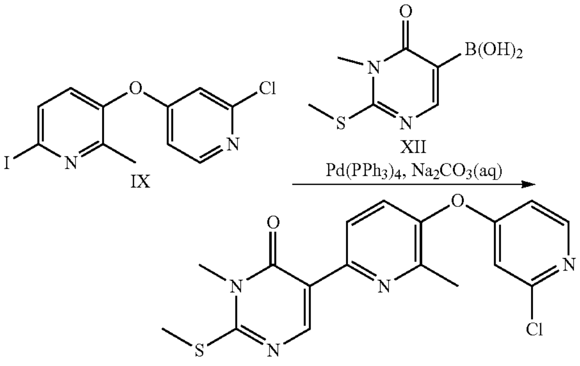

IV 5-(5-((2-chloropyridin-4-yl)oxy)-6-methylpyridin-2-yl)-3-methyl-2-(methylthio)pyrimidin-4(3H)-one (IV): 3-((2-chloropyridin-4-yl)oxy)-6-iodo-2-methylpyridine (IX)(1.00 kg), (1-methyl-2-(methylthio)-6-oxo-1,6-dihydropyrimidin-5-yl)boronic acid (XII)(0.64 kg), palladium-tetrakis(triphenylphosphine) (0.10 kg) and dioxane (15.3 L) were charged in a reactor, and the mixture was de-gassed by sparging nitrogen. In a separate vessel, a solution of sodium carbonate (0.92 kg) in deionized water (3.1 L) was prepared. The sodium carbonate solution was transferred to the reactor, and the mixture was de-gassed by sparging nitrogen. The resulting reaction mixture was heated at reflux for about 3 hours, cooled to 15-25° C. and quenched with deionized water and filtered. The filter cake was washed with deionized water. A suspension of the wet solid in deionized water was heated to 35-45° C., cooled to 15-25° C., then filtered again, washed with deionized water and dried under vacuum at a temperature of not more than 50° C. The resulting solid was taken up in methyl-tert-butyl ether (10.1 L). The mixture was stirred at 45-55° C., cooled to 15-25° C., and filtered. The filter cake was washed with methyl-tert-butyl ether and dried at a temperature not more than 40° C. under vacuum. The title compound was obtained in a yield of 82% (0.89 kg).

Example 1c. Preparation of a Compound of Formula (III)

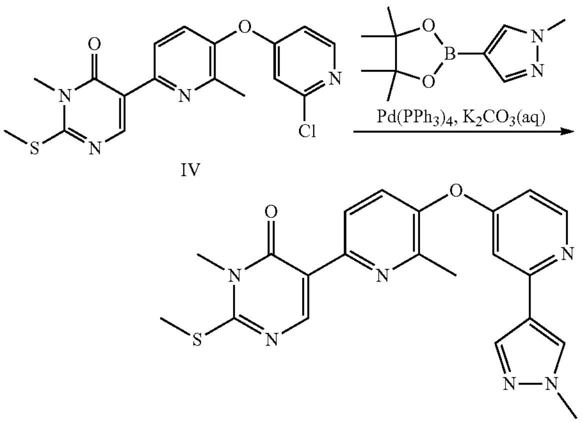

III 3-methyl-5-(6-methyl-5-((2-(1-methyl-1H-pyrazol-4-yl) pyridin-4-yl)oxy)pyridin-2-yl)-2-(methylthio)pyrimidin-4 (3H)-one (III): 5-(5-((2-chloropyridin-4-yl)oxy)-6-methylpyridin-2-yl)-3-methyl-2-(methylthio)pyrimidin-4(3H)-one (IV)(1.00 kg), 1-methyl-4-(4,4,5,5-tetramethyl-1,3,2-dioxaborolan-2-yl)-1H-pyrazole (0.83 kg), palladium-tetrakis(triphenyl phosphine) (0.11 kg), and dioxane (12.0 L) were charged to a reactor, and the mixture was de-gassed by sparging nitrogen. Then, a potassium carbonate solution (1.48 kg) in deionized water (4.0 L) was added to the reactor, and the mixture was de-gassed by sparging nitrogen. The mixture was heated to reflux for about 15 hours, then cooled to 15-25° C., quenched with deionized water and stirred. The precipitated solid was filtered, washed with deionized water, and partially dried on filter. The solid was then charged in a vessel, together with deionized water and heated at 35-45° C., then cooled to 15-25° C., filtered, washed with deionized water, and dried with vacuum at a jacket temperature of not more than 40° C. The solid was re-charged in a vessel in isopropyl alcohol (5.0 L) and acetone (2.5 L) and was heated to 65-75° C., then cooled and stirred at 5-15° C., filtered, and washed with isopropyl alcohol. The wet solid was re-charged in the vessel with isopropyl alcohol (5.0 L) and acetone (2.5 L). The mixture was then heated at 65-75° C., then cooled and stirred at 5-15° C., filtered, and washed with isopropyl alcohol. The solid was dried under vacuum at a temperature lower than, or equal to, 40° C. The title compound was obtained in a yield of 66% (0.74 kg).

Example 1d. Preparation of a Dihydrate of Compound of Formula (II)

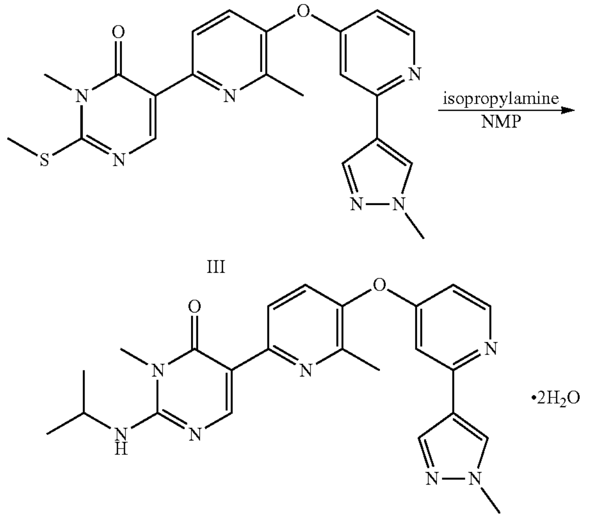

II 2-(isopropylamino)-3-methyl-5-(6-methyl-5-((2-(1-methyl-1H-pyrazol-4-yl)pyridin-4-yl)oxy)pyridin-2-yl)pyrimidin-4(3H)-one (II): 3-methyl-5-(6-methyl-5-((2-(1-methyl-1H-pyrazol-4-yl)pyridin-4-yl)oxy)pyridin-2-yl)-2-(methylthio)pyrimidin-4(3H)-one (III)(1.00 kg), isopropylamine (8.1 L), and N-methylpyrrolidone (8.1 L) were charged in a reactor, heated to 105-115° C. for about 28 hours in a sealed environment. The reaction mixture was cooled to 20-30° C. Distillation was performed under vacuum with a jacket temperature of not more than 35° C. until no more distillate was collected, then the temperature was adjusted to 15-25° C. Deionized water was added and the mixture was stirred at 15-25° C. The solid was isolated by filtration, washed with deionized water, and dried at a jacket temperature of not more than 40° C. The dried product and methyl-tert-butyl ether were stirred and then filtered and the solid was washed with methyl-tert-butyl ether. The solid was then charged in a reactor, together with dichloromethane and methanol and the mixture was stirred to obtain a clear solution. 3-Mercaptopropyl ethyl sulfide Silica was charged in the reactor and the reactor contents were stirred for about 17.5 hours. The mixture was filtered, followed by a rinse with dichloromethane, and the treatment was repeated with a fresh portion of 3-mercaptopropyl ethyl sulfide Silica. The filtered content was distilled under vacuum until minimum volume, and the distillation was repeated with a continuous addition of acetone while maintaining the volume. The resulting residue was diluted with a mixture of acetone and water and stirred and heated to 50° C., followed by cooling. The solid was isolated by filtration and washed with a mixture of acetone and water. The resuspension in acetone and water was repeated, and the resulting solid was dried under vacuum with heat. The solid was dispensed into a vessel. DMAc (dimethylacetamide) and water were charged to the vessel to give 5 volumes of DMAc-$H_2O$ (4.25 volumes DMAc and 0.75 volumes $H_2O$) ratio. The system was stirred to give complete suspension of material and heated to about 80° C. to access clear solution. The system was then cooled to about 65° C. and held for about 15 minutes. Milled seed material of the dihydrate of the compound of Formula (II) (about 5 wt. % of the weight of the compound of Formula (II)) was charged to the vessel. The system was held for 15-60 minutes. Water (2 volumes) was charged to the vessel at 65° C. over about 4 hours (0.5 volumes/hour). The system was allowed to cool to about 25° C. at about 0.1° C./min over about 6.5 hours before the mixture was stirred at room temperature for about 5 hours. The solid precipitate was isolated via filtration, washed with water (about 10 volumes then about 5 volumes) and dried under vacuum at a temperature no higher than 40° C. until moisture content by Karl Fischer analysis (KF) was no more than about 8% and no less than about 6% as shown in Table 5. The title compound was obtained in a yield of 70% (0.78 kg).

Example 2. Exemplary Batches of Compounds of Formula (IX), (IV), (III), and (II)

Tables 1-4 provide the results of ultra-high-performance liquid chromatography (UHPLC) analysis of exemplary batches of compounds prepared according to Example 1. Representative UHPLC conditions: Column Acquity UPLC CSH C18, 1.7 μm, 2.1 mm×100 mm, or equivalent. Mobile Phase (MP) A: 10.5 mM Ammonium Formate pH 3.5. MP B: acetonitrile. In Table 1 to Table 4 below, "area %" refers to the percentage of area under the curve of a peak out of the total area under the curve of all peaks in the ultra-high-performance liquid chromatography (UHPLC) analysis.

Table 1 shows the results of a UHPLC analysis of exemplary batches of a compound of Formula (IX) prepared according to Example 1a.

TABLE 1

| | Batches | | |
|---|---|---|---|
| Compound | 1a (area %) | 1b (area %) | 1c (area %) |
| VIII | 0.10 | 0.08 | 0.07 |
| IX | 99.6 | 99.8 | 99.8 |
| XI | 0.07 | 0.05 | 0.05 |
| XIII | <0.05 | <0.05 | <0.05 |
| XVII | 0.11 | <0.05 | <0.05 |
| XVIII | <0.05 | <0.05 | <0.05 |

Table 2 shows the results of a UHPLC analysis for exemplary batches of a compound of Formula (IV) prepared according to Example 1b.

TABLE 2

| | Batches | | |
|---|---|---|---|
| Compound | 1a (area %) | 1b (area %) | 1c (area %) |
| IV | 99.5 | 99.2 | 99.7 |
| XIX | <0.07 | <0.07 | <0.07 |
| XX | <0.07 | <0.07 | 0.07 |

Table 3 shows the results of a UHPLC analysis for exemplary batches of a compound of Formula (III) prepared according to Example 1c.

TABLE 3

| | Batches | | |
|---|---|---|---|
| Compound | 1a (area %) | 1b (area %) | 1c (area %) |
| III | 99.0 | 99.0 | 99.4 |
| IV | <0.05 | <0.05 | <0.05 |
| XX | <0.05 | <0.05 | <0.05 |
| XIX | 0.36 | 0.42 | 0.31 |
| XXI | 0.41 | 0.17 | 0.13 |

Table 4 shows the results of a UHPLC analysis for exemplary batches for a dihydrate of the compound of Formula (II) prepared according to Example 1d.

TABLE 4

| | Batches | | |
|---|---|---|---|
| Compound | 1a (area %) | 1b (area %) | 1c (area %) |
| II | 99.5 (% w/w) | 99.1 (% w/w) | 99.4 (% w/w) |
| III | 0.10 | 0.14 | 0.07 |
| XXI | 0.05 | <0.05 | <0.05 |
| XXII | <0.05 | <0.05 | <0.05 |
| XXIII | 0.14 | 0.16 | 0.08 |

Table 5 shows the results for moisture content as determined by Karl Fischer analysis (KF) for exemplary batches for a dihydrate of the compound of Formula (II) prepared according to Example 1d.

TABLE 5

| | Batches | | |
|---|---|---|---|
| Compound | 1a % | 1b % | 1c % |
| water | 7.8 | 7.5 | 7.7 |

Table 1a shows the results of a UHPLC analysis of exemplary batches of a compound of Formula (IX) prepared according to Example 1a.

TABLE 1a

| | Batches | | |
|---|---|---|---|
| Compound | 1a (AUC) | 1b (AUC) | 1c (AUC) |
| VIII | 0.10 | 0.08 | 0.07 |
| IX | 99.6 | 99.8 | 99.8 |
| XI | 0.07 | 0.05 | 0.05 |
| XIII | <0.05 | <0.05 | <0.05 |

TABLE 1a-continued

| | Batches | | |
|---|---|---|---|
| Compound | 1a (AUC) | 1b (AUC) | 1c (AUC) |
| XVII | 0.11 | <0.05 | <0.05 |
| XVIII | <0.05 | <0.05 | <0.05 |

Table 2a shows the results of a UHPLC analysis for exemplary batches of a compound of Formula (IV) prepared according to Example 1b.

TABLE 2a

| | Batches | | |
|---|---|---|---|
| Compound | 1a (AUC) | 1b (AUC) | 1c (AUC) |
| IV | 99.5 | 99.2 | 99.7 |
| XIX | <0.07 | <0.07 | <0.07 |
| XX | <0.07 | <0.07 | 0.07 |

Table 3a shows the results of a UHPLC analysis for exemplary batches of a compound of Formula (III) prepared according to Example 1c.

TABLE 3a

| | Batches | | |
|---|---|---|---|
| Compound | 1a (AUC) | 1b (AUC) | 1c (AUC) |
| III | 99.0 | 99.0 | 99.4 |
| IV | <0.05 | <0.05 | <0.05 |
| XX | <0.05 | <0.05 | <0.05 |
| XIX | 0.36 | 0.42 | 0.31 |
| XXI | 0.41 | 0.17 | 0.13 |

Table 4a shows the results of a UHPLC analysis for exemplary batches for a dihydrate of the compound of Formula (II) prepared according to Example 1d.

TABLE 4a

| | Batches | | |
|---|---|---|---|
| Compound | 1a (AUC) | 1b (AUC) | 1c (AUC) |
| II | 99.5 (% w/w) | 99.1 (% w/w) | 99.4 (% w/w) |
| III | 0.10 | 0.14 | 0.07 |
| XXI | 0.05 | <0.05 | <0.05 |
| XXII | <0.05 | <0.05 | <0.05 |
| XXIII | 0.14 | 0.16 | 0.08 |

EQUIVALENTS

Those skilled in the art will recognize or be able to ascertain using no more than routine experimentation, numerous equivalents to the specific embodiments described specifically in this disclosure. Such equivalents are intended to be encompassed in the scope of the following claims.

We claim:

1. A dihydrate form of the compound of Formula (II):

(II)

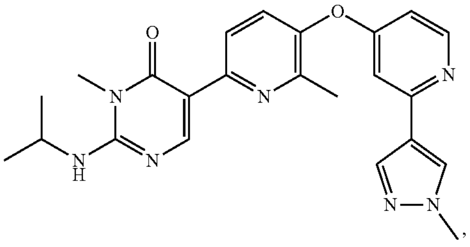

prepared by a process comprising:

reacting a compound of Formula (IX):

(IX)

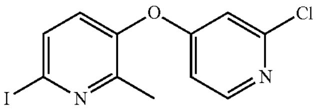

with a compound of Formula (XII):

(XII)

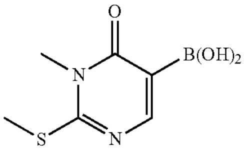

in the presence of a first catalyst to produce a compound of Formula (IV):

(IV)

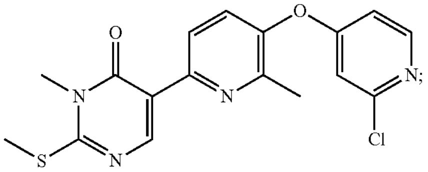

reacting the compound of Formula (IV) with a compound represented by:

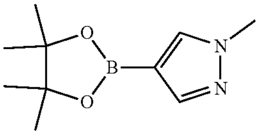

in the presence of a second catalyst, to produce a compound of Formula (III):

(III)

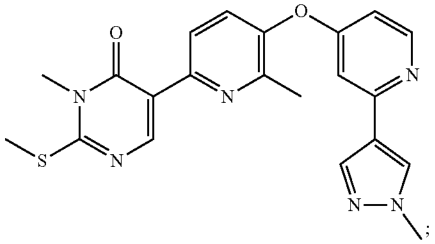

and reacting the compound of Formula (III) with isopropylamine, thereby preparing the compound of Formula (II).

2. A pharmaceutical composition, comprising the dihydrate form of claim 1 and a pharmaceutically acceptable excipient.

3. The dihydrate form of claim 1, wherein the first catalyst is a palladium catalyst.

4. The dihydrate form of claim 1, wherein the first catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$.

5. The dihydrate form of claim 1, wherein the first catalyst is $Pd(PPh_3)_4$.

6. The dihydrate form of claim 1, wherein the second catalyst is a palladium catalyst.

7. The dihydrate form of claim 1, wherein the second catalyst is selected from the group consisting of $Pd(PPh_3)_4$, $Pd(OAc)_2$/SPhos, $Pd(dppf)Cl_2$, $Pd(dppf)Cl_2$·DCM, XPhos Pd G2, and $Pd_2(dba)_3$.

8. The dihydrate form of claim 1, wherein the second catalyst is $Pd(PPh_3)_4$.

* * * * *